US010843824B2

(12) United States Patent
Stultz et al.

(10) Patent No.: US 10,843,824 B2
(45) Date of Patent: Nov. 24, 2020

(54) SYRINGE POSITIONING APPARATUS AND METHOD

(71) Applicant: BAXTER CORPORATION ENGLEWOOD, Englewood, CO (US)

(72) Inventors: Tammy Stultz, Westminster, CO (US); David Lee Holien, Parker, CO (US); Sophoeun Svai, Thornton, CO (US); Yuriy Konstantinovich Umanskiy, Centennial, CO (US); Brian William Ward, Littleton, CO (US); Roy Sven Hovland, Denver, CO (US); James Robert Hutchison, Denver, CO (US); Joshua Nathan Aumiller, Lakewood, CO (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 16/067,374

(22) PCT Filed: Dec. 22, 2016

(86) PCT No.: PCT/US2016/068227
§ 371 (c)(1),
(2) Date: Jun. 29, 2018

(87) PCT Pub. No.: WO2017/116955
PCT Pub. Date: Jul. 6, 2017

(65) Prior Publication Data
US 2019/0009935 A1 Jan. 10, 2019

Related U.S. Application Data

(60) Provisional application No. 62/272,786, filed on Dec. 30, 2015.

(51) Int. Cl.
B65B 3/00 (2006.01)
A61M 5/178 (2006.01)
A61M 5/00 (2006.01)

(52) U.S. Cl.
CPC ............. B65B 3/003 (2013.01); A61M 5/008 (2013.01); A61M 5/1782 (2013.01)

(58) Field of Classification Search
CPC ...... B65B 3/003; A61M 5/008; A61M 5/1782
(Continued)

(56) References Cited

U.S. PATENT DOCUMENTS 2,695,642 A * 11/1954 White ..................... A47J 43/26
99/572
4,523,474 A * 6/1985 Browne ................ G01L 9/0072
361/283.4
(Continued)

OTHER PUBLICATIONS

International Search Report and Written Opinion dated Apr. 11, 2017 in corresponding PCT Application No. PCT/US2016/068227.

Primary Examiner — Lynn E Schwenning
(74) Attorney, Agent, or Firm — K&L Gates LLP

(57) ABSTRACT

Syringe positioning apparatus and methods are disclosed that provide for automated positioning of a syringe at an axially aligned position on a predetermined axis. The apparatus and methods employ first and second members having opposing surfaces that include first and second ramps, respectively, wherein the first ramp angles upward and away from the second member, and the second ramp angles upward and away from the first member. At least one of the first and second members may be advanceable toward the other by an actuator, wherein the first and second ramps may slidably engage a syringe and thereby elevate the syringe to the axially aligned position on the predetermined axis.

29 Claims, 18 Drawing Sheets

(58) Field of Classification Search
USPC .................................................. 269/55, 56
See application file for complete search history.

(56) References Cited

U.S. PATENT DOCUMENTS

| | | | | |
|---|---|---|---|---|
| 5,230,599 | A * | 7/1993 | Orr | B66F 9/18 |
| | | | | 212/243 |
| 5,523,941 | A * | 6/1996 | Burton | B23Q 1/623 |
| | | | | 269/73 |
| 5,584,814 | A * | 12/1996 | Schuster | B65B 3/003 |
| | | | | 222/326 |
| 5,588,796 | A * | 12/1996 | Ricco | B25J 9/1679 |
| | | | | 294/100 |
| 6,427,995 | B1 * | 8/2002 | Steinwall | B25B 1/2405 |
| | | | | 269/283 |
| 9,517,895 | B2 * | 12/2016 | Bacalia | B25J 9/1682 |
| 2004/0104243 | A1 * | 6/2004 | Osborne | B65B 3/003 |
| | | | | 222/63 |
| 2005/0220639 | A1 * | 10/2005 | Sasaki | A61M 5/1458 |
| | | | | 417/415 |
| 2006/0000370 | A1 * | 1/2006 | Poursayadi | A23N 5/00 |
| | | | | 99/568 |
| 2007/0191770 | A1 * | 8/2007 | Moberg | A61M 5/14566 |
| | | | | 604/131 |
| 2010/0187737 | A1 * | 7/2010 | Marrinan | B23Q 1/037 |
| | | | | 269/56 |
| 2012/0048676 | A1 * | 3/2012 | Giribona | B65B 3/003 |
| | | | | 198/346.2 |
| 2014/0183806 | A1 * | 7/2014 | Krulj | B24B 5/50 |
| | | | | 269/55 |

* cited by examiner

SYRINGE POSITIONING APPARATUS AND METHOD

CROSS REFERENCES TO RELATED APPLICATIONS

The present application is a national stage of International Application No. PCT/US2016/068227 filed on Dec. 22, 2016 which claims priority to U.S. Patent Application No. 62/272,786, filed on Dec. 30, 2015, entitled "SYRINGE POSITIONING APPARATUS AND METHOD", which application is incorporated herein by reference in its entirety. This application relates to and incorporates by reference the co-owned U.S. Patent Application No. 62/272,789, filed on Dec. 30, 2015, entitled "MEASUREMENT OF SYRINGE GRADUATION MARKS USING A VISION SYSTEM". This application relates to and incorporates by reference the co-owned application U.S. Patent Application No. 62/272,794, filed on Dec. 30, 2015, entitled "CAPACITIVE SINGLE PLATE BUBBLE DETECTOR". This application relates to and incorporates by reference the co-owned U.S. patent application Ser. No. 14/984,022, filed on Dec. 30, 2015, entitled "SOURCE FLUID INLET ASSEMBLY FOR AUTOMATED FILLING DEVICE". This application relates to and incorporates by reference the co-owned U.S. Patent Application No. 62/272,798, filed on Dec. 30, 2015, entitled "SYRINGE GRIPPING APPARATUS AND METHOD". This application relates to and incorporates by reference the co-owned U.S. patent application Ser. No. 14/984,285, filed on Dec. 30, 2015, entitled "SYRINGE PLUNGER POSITION APPARATUS AND METHOD". This application relates to and incorporates by reference the co-owned U.S. Patent Application No. 62/272,816, filed on Dec. 30, 2015, entitled "INLET TUBE SET FOR SOURCE INGREDIENT DELIVERY". This application relates to and incorporates by reference the co-owned U.S. patent application Ser. No. 14/984,913, filed on Dec. 30, 2015, entitled "TIP CAP FOR AUTOMATIC SYRINGE FILING APPARATUS". This application relates to and incorporates by reference the co-owned U.S. patent application Ser. No. 15/179,643, filed on Jun. 10, 2016, entitled "TAMPER EVIDENT CAP". This application relates to and incorporates by reference the co-owned U.S. patent application Ser. No. 15/360,635, filed Nov. 23, 2016, entitled "LABEL APPLICATOR FOR SYRINGE LABELING".

BACKGROUND

Syringes are employed to dispense a variety of flowable materials, including therapeutic, diagnostic and other materials utilized in medical applications. In that regard, it is typical to utilize a syringe of a size that generally corresponds with a predetermined amount of material to be dispensed or to otherwise be available for dispensation in a given procedure. For example, in medical applications such amount may be established pursuant to prescription or industry practice, and may significantly vary depending upon the given intended use. In turn, a wide range of syringe sizes are utilized by medical care providers.

Until recently, syringe filling was largely completed manually. In medical applications, such manual filling has typically been completed in pharmacies by highly-trained personnel, including pharmacies located at patient care provider sites having space constraints (e.g. a hospital pharmacy).

Increasingly, attempts have been made to automate one or more steps associated with syringe filling. Such automation may be desirable for a number of reasons, including for example cost efficiencies and quality control. However, such attempts have confronted a number of challenges.

In particular, automated systems typically require automated positioning of syringes at one or more predetermined locations with a high degree of accuracy, on a repeatable and reliable basis. To address such requirements, known automated systems have utilized complex componentry that has restricted the ability to efficiently handle syringes of different sizes. Further, in typical medical-related applications, syringe handling may necessarily require a sterile environment that often entails the use of a vented enclosure, thereby further compounding space constraints in typical pharmacy settings.

SUMMARY

The present disclosure addresses the above-noted challenges to provide improved apparatus and methods for automated syringe positioning.

In disclosed embodiments, a syringe positioning apparatus is disclosed that includes a first member having an upstanding, first surface, and a second member having an upstanding, second surface facing the first surface of the first member. The first and second surfaces may include first and second ramps, respectively, that angle upward and away from one another. At least one of the first and second members may be advanceable toward the other one, wherein upon such advancement the first and second surfaces are operable to slidably engage, elevate and thereby locate a syringe in an axially aligned position on a predetermined axis extending between the first and second members.

As may be appreciated the relative advancement of opposing first and second ramps that angle upward and away from one another yields an elegant approach for effectively lifting a syringe to and retaining the syringe at a desired location on a predetermined axis to facilitate additional syringe handling procedures, (e.g. purging, filling, labeling, etc.) Further, elevated syringe positioning may be achieved with syringe engagement that is advantageously limited to opposing ends of a syringe. That is, the disclosed approach avoids a need for syringe barrel engagement to achieve elevated positioning on a predetermined axis. In turn, the disclosed approach advantageously provides a syringe positioning apparatus that may be utilized to position syringes having a wide range of different lengths and diameters at a desired location on a predetermined axis. For example, in medical-related applications, disclosed syringe positioning apparatus may be employed to position syringes having a range of lengths of about 7.5 cm to 17 cm, e.g. to dispense flowable material volumes across a range of about 1 mL to about 60 mL. Further, the disclosed automated syringe positioning approach facilitates implementation in relatively compact arrangements, thereby accommodating pharmacy implementations.

In contemplated embodiments, the predetermined axis for syringe positioning may be located in a first horizontal plane. Further, the first member may be linearly advanceable along a longitudinal axis toward the second member, wherein the longitudinal axis may be located in a second horizontal plane below the first horizontal plane. Additionally, the predetermined axis for syringe positioning and the longitudinal axis for first member advancement may be located in parallel relation.

The disclosed syringe positioning apparatus may be utilized to position syringes with caps or no caps on the dispensing tips thereof. In some implementations, the syringe positioning apparatus may be provided to position syringes having locating caps on the dispensing tips thereof, as will be further described.

In some embodiments, the syringe positioning apparatus may comprise an actuator to linearly advance the first member toward and retract the first member away from the second member. The actuator may include a motor having a controller to automatically control a speed of the motor. In turn, the motor may be operated to provide a mechanical output to advance the first member until the motor stalls, whereupon the controller may automatically terminate operation of the controller and the actuator may maintain the first member at a corresponding advanced position. The motor controller may be provided so that, upon advancement of the first member toward the second member, a syringe may be supportably engaged and restrainably located in an axially aligned position on the predetermined axis between the first and second members while maintaining an axial compression force applied to the syringe within a predetermined pressure range (e.g. within a range of about 5N to about 20N). Such approach facilitates automated positioning of syringes having a range of different lengths.

In some implementations, the actuator may be operable to provide an output indicative of a length of a syringe that is located in an axially aligned position on the predetermined axis. For example, the actuator may include a motor operable to provide an output indicative of a length of travel of the first member from a predetermined home position to a position at which a syringe is positioned between the first and second members in an axially aligned position on the predetermined axis, with an end of the syringe engaged with the second member at a predetermined or determinable location.

In some embodiments, the first surface of the first member may include a first limiting portion that extends upward from the first ramp to define a first concave region. Similarly, the second surface of the second member may include a second limiting portion that extends upward from the second ramp thereof to define a second concave region. The first and second concave regions of the first and second members, respectively, may function to limit and otherwise direct the travel of the ends of a syringe positioned between the first and second members.

In some implementations the first and second ramps of the first and second members, respectively, may be defined by corresponding, inclined first and second channels that are oriented to direct a syringe slidably engaged thereby upward towards an axially aligned position on the predetermined axis (e.g. in a funnel-like manner). By way of example, the first and/or second channels may have a corresponding longitudinal axis that lie in a vertical plane with the predetermined axis. The first and second channels may comprise arcuate, concave surfaces that extend along their respective longitudinal axis. In some implementations, the first and second members may include first and second channels, respectively, having corresponding parabolic configurations that conformally adjoin the conical first portions of the first and second surfaces, respectively.

Optionally, the first member and/or second member may include an upwardly angled groove that extends within and along at least a portion the corresponding first channel and/or second channel. The upwardly angled groove(s) may be provided to further direct an end of the syringe to an axially aligned position on the predetermined axis. In particular, when a locating cap is provided at an end of a syringe, a groove may be provided in the second member so that a peripheral rim of the locating cap may slidably engage and travel upward and along opposing side edges of the groove in a rail-like manner. For example, the second member may include a groove having an elongated diamond configuration.

In some arrangements, the first surface of the first member may include a first conical configuration centered on and advanceable along the predetermined axis. Further, the second surface of the second member may include a first portion having a second conical configuration centered on the predetermined axis. As may be appreciated, the conical first portions of the first and second surfaces of the first and second members may facilitate positioning of a syringe in an axially aligned position on the predetermined axis. In one approach the second member may include an upwardly angled groove that extends within and along at least a portion of the second channel with a top end located within the conical first portion of the second member.

In contemplated embodiments, a syringe positioning apparatus may include a tray defining a recession that extends from the second member towards and under the first member, wherein the tray may support a syringe in a reclined position within the recession, wherein the first member is advanceable by an actuator over and along the recession towards the second member. The recession may have a V-shaped configuration with a longitudinal axis that extends substantially parallel to the predetermined axis for syringe positioning. In that regard, the V-shaped recession may facilitate orientation of a syringe located therein in aligned relation to the longitudinal axis. Further, the V-shaped recession may be provided so that the longitudinal axis thereof lies in a vertical plane with the predetermined axis.

In some embodiments, the tray may include a bottom slot that extends along a length of the recession of the tray to a base of the second member. Further, the first member may include a projection that extends in to and is advanceable along at least a portion of the slot upon advancement of the first member towards the second member. The provision of the noted tray slot and first member projection facilitates advancement of smaller syringes into sliding engagement with the second member during syringe positioning.

As indicated, capped or uncapped syringes may be positioned utilizing the disclosed syringe positioning apparatus. Relatedly, in some embodiments, the second member may include an aperture located on the predetermined axis and sized to receive one of a dispensing tip of a syringe and a projecting tip of a locating cap located on a dispensing tip of a syringe, wherein the second surface of the second member may extend about at least a portion of the aperture. In some implementations, the aperture may be located within a conical first portion of the second surface of the second member. In one approach, an upwardly angled groove provided in the second member may extend from the base thereof to a top end that adjoins the aperture.

In some embodiments, a syringe positioning apparatus may include a first member that is advanceable by an actuator towards a second member, wherein first and second surfaces of the first and second members, respectively, include corresponding, opposing ramps that are operable to slidably engage and thereby elevate opposing ends of a syringe to an axially aligned position on a predetermined axis extending between the first and second members, and wherein the apparatus further includes a sensor for sensing the positioning of one of a dispensing tip and a projecting tip of a locating cap located on a dispensing tip at one end of a syringe when such end is located within an aperture of the second member.

In such embodiments, the sensor may provide an output signal in response to positioning of a syringe dispensing tip or a projecting tip of a locating cap located on a syringe dispensing tip, within the aperture. In that regard, the output signal may be indicative of the presence of one of a syringe dispensing tip and a projecting tip of a locating cap when positioned at a predetermined location within the aperture of the second member. Such predetermined location may function as a reference datum for syringe length determination and for additional syringe handling procedures to be completed after positioning of a syringe at an axially aligned position on the predetermined axis (i.e. with one end of the syringe located at the predetermined location).

In some implementations, the sensor may comprise a capacitive sensor for sensing an electrical capacitance that is dependent upon a position of one of a syringe dispensing tip and a projecting tip of a locating cap located on a syringe dispensing tip, relative to the aperture of the second member. In contemplated embodiments the capacitive sensor may comprise first and second conductive surfaces, and the sensor may include a rod member having a first end located at the aperture (e.g. at the predetermined location for syringe end positioning), and a second end located to displace one of the first and second conductive surfaces upon positioning of one of a syringe dispensing tip and a projecting tip of a locating cap, within the aperture of the second member. In one approach, the second conductive surface may be provided on a leaf spring member that is biased toward the first conductive surface, and the second end of the rod member may be positioned so that the spring member biases the first end of the rod member to a position at the predetermined location, or reference datum, for syringe end positioning. In turn, when the syringe dispensing tip or projection tip of a locating cap is located at the predetermined location, the rod member is displaced, thereby displacing the second conductive surface.

In some embodiments, the output signal may be indicative of the presence of one of a syringe dispensing tip and a projecting tip of a locating cap when positioned at a location different from the above-noted predetermined location within the aperture. In turn, in response to such output signal, the actuator may be provided to automatically retract the first member away from the second member, thereby allowing a syringe to drop back in to the tray, e.g. for a repeated attempt at positioning on the predetermined axis or removal from the tray.

In some embodiments, the syringe positioning apparatus may include a mount member operatively interconnected to the actuator and moveable along the tray in a first direction from a retracted position toward the second member and in a second direction away from the second member toward the retracted position, wherein the first member may be supportably interconnected to and moveable with the mount member. The mount member and first member may be provided so that, during movement of the mount member in the first direction from the retracted position, the first member is disposed to pass through a first region of the tray to engage and thereby advance a syringe located within the first region into a second region of the tray within which the first member and second member are then operable to engage, elevate and thereby locate the syringe on the predetermined axis therebetween, as described above. Further, the mount member and first member may be provided so that, during movement of the mount member in the second direction toward the retracted position, the first member may retract away from the second member and be disposed to bypass the first region of the tray. In the later regard, such bypass of the first region of the tray facilitates the successive positioning of syringes in the first region of the tray and contemporaneous positioning of syringes on the predetermined axis in the second region of the tray.

In some implementations the first member may be moveable relative to the mount member and disposed to move from a first orientation to a second orientation for bypassing the first region of the tray during movement of the mount member in the second direction. In that regard, the syringe positioning apparatus may further comprise a guide member disposed to guide the first member in said second orientation for bypass of the first region of the tray during movement of the mount member in the second direction.

Further, the guide member may be disposed to guide the first member to the first orientation from the second orientation after said bypass of the first region during movement of the mount member in the second direction. Additionally, in some embodiments, the guide member may be disposed to guide the first member in said first orientation for passage through the first region and in to the second region during movement of the mount member in the first direction.

In some implementations, the first member may be pivotably interconnected to the mount member and disposed to pivot from the first orientation to the second orientation to bypass the first region during movement of the mount member in the second direction, and to pivot from the second orientation to the first orientation after bypassing the first region during movement of the mount member in the second direction. In that regard, the guide member may be disposed to guide the first member in the second orientation for bypass of the first region during movement of the mount member in the second direction, and to guide pivotal movement of the first member to the first orientation from the second orientation after bypass of the first region during movement of the mount member in the second direction.

In some arrangements, the first member may be pivotably interconnected to the mount member at a pivot axis elevated relative to the tray, wherein the first member may be pivoted downward in said first orientation and pivoted upward in the second orientation. In such arrangements, the syringe positioning apparatus may further include a carrier member supportably and pivotably interconnected to the mount member at the pivot axis, wherein the first member is interconnected in fixed relation to the pivot member for pivotable co-movement therewith.

In the later regard, the carrier member may comprise at least one guide follower. In turn, the guide member may comprise a first guide track to interface with the guide follower(s) to guide the first member in the first orientation for passage through the first region and in to the second region relative to the tray during movement of the mount member in the first direction. Additionally, the guide member may further comprise a second guide track to interface with the guide follower(s) to guide the first member in the second orientation for bypass of the first region during movement of the mount member in the second direction, and to guide pivotal movement of the first member to the first orientation from the second orientation after the bypass of the first region during movement of the mount member in the second direction.

In some implementations, the syringe positioning apparatus may further include a diverter member to divert, or guide, the guide follower(s) to interface with the second guide track during movement of the mount member from the second region in the second direction toward the retracted position. In that regard, the diverter member may be disposed to be pivotable relative to the guide member so as to pivot from a first position to a second position during engagement with the guide follower during movement of the mount member in the first direction from the retracted position, and to maintain the first position during engagement with the guide follower(s) during movement of the mount member in the second direction toward the retracted position. In that regard, the diverter member may include a ramped surface to engage and thereby elevate the guide member(s) during movement of the mount member in the second direction.

In further embodiments, an automated syringe positioning method is disclosed that comprises advancing at least one of a first member and a second member toward the other, with a syringe located therebetween, wherein the first and second members have upstanding first and second surfaces, respectively, facing one another and including first and second ramps, respectively, that angle upward and away from one another. The method may further include engaging first and second ends of the syringe with the first and second ramps, respectively, during the advancing step to elevate and thereby locate the syringe in an axially aligned position on a predetermined axis extending between the first and second members. As may be appreciated, the first and second ramps facilitate sliding engagement with the first and second ends of the syringe for gradual movement upward to the elevated, axially aligned position on the predetermined axis.

In some embodiments, the advancing may include utilizing an actuator to linearly advance the first member towards the second member. In some implementations, the actuator may include a motor having a controller to automatically control a speed of the motor. In turn, the motor may be operated to provide a mechanical output to advance the first member until the motor stalls, whereupon the controller automatically terminates operation of the controller and the actuator maintains the first member at a corresponding advanced position. The motor controller may be provided so that, upon advancement of the first member toward the second member, a syringe may be supportably engaged and restrainably located in an axially aligned position on the predetermined axis between the first and second members while maintaining an axial compression force applied to the syringe within a predetermined pressure range (e.g. within a range of about 5N to about 20N). Such approach facilitates automated positioning syringes having a range of different lengths.

In some implementations, method embodiments may further include providing an output indicative of a length of a syringe upon positioning of the syringe in an axially aligned position on the predetermined axis. In some approaches, the output may be provided by the actuator and may be further indicative of a position of the first member relative to a predetermined reference location upon positioning of the syringe in the axially aligned position on the predetermined axis.

In some embodiments, the first and second ramps may be at least partially defined by corresponding inclined first and second channels, respectively. In turn, the engaging step may comprise utilizing the first and second channels to direct the first and second ends of the syringe upward toward the axially aligned position on the predetermined axis. In some arrangements, the first surface of the first member may include a first portion having a first conical configuration centered on the predetermined axis and the second surface of the second member may include a first portion having a second conical configuration centered on the predetermined axis. In turn, the engaging step may further include employing the conical portions of the first and second surfaces, respectively, to center the first and second ends of the syringe on the predetermined axis.

In some embodiments, the method may further include receiving and supporting the syringe in a tray defining a V-shaped recession that extends from the second member toward the first member, wherein during the advancing step the first member is advanced over and along the V-shaped recession towards the second member. In that regard, the first member may engage the first end of the syringe to slidably advance the syringe along the tray towards the second member and into engagement with the second member. Upon further advancement of the first member, the syringe may be positioned in the axially aligned position on the predetermined axis, with the first end thereof located at the above-referenced, predetermined location.

In some method implementations, the first member may be supportably interconnected to a mount member that is moveable along the tray in a first direction from a retracted position toward the second member and in a second direction toward the retracted position. In turn, the advancing step may include first moving the mount member in the first direction from the retracted position, wherein the first member may be disposed to pass through a first region of the tray to engage and thereby advance a syringe from the first region in to a second a region of the tray within which the first member and second member engage, elevate and thereby locate the syringe on the predetermined axis.

In conjunction with such implementations, the method may further include second moving the mount member in the second direction toward the retracted position, wherein the first member may be disposed to bypass the first region of the tray. In that regard, the first member may be moveable relative to the mount member and disposed in a first orientation during the first moving step, wherein the method may further include moving the first member from the first orientation to a second orientation during the second moving step for the bypass of the first region. In that regard, the moving step may include guiding the first member from the first orientation to the second orientation for the bypass of the first region. Further, the moving step may include moving the first member from the second orientation to the first orientation after the bypass of the first region. In turn, the guiding step may further include guiding the first member from the second orientation to the first orientation after the bypass of the first region. As may be appreciated, each of the guiding steps may be facilitated via the utilization of a guide member having one or more guide tracks to guide and thereby orient the first member during movement thereof in the first direction and second direction.

In further disclosed embodiments, a syringe loading and transfer apparatus is also provided that includes a loading member for supportably receiving one or a plurality of syringes, a support member for receiving a syringe from the loading member at a first position and transferring the syringe from the first position in a first direction, and a tray for supportably receiving the syringe from the support member after the support member is moved from the first position in the first direction. In some implementations, the loading member may comprise a channel for supportably receiving a cap located on a dispensing tip of a capped syringe at a first end of the channel, wherein the capped syringe is supportably suspended from the channel. Further, the support member may be provided to supportably receive the cap of the capped syringe from the loading member at the first position adjacent to a second end of the channel, wherein the support member is moveable to transfer the capped syringe from the first position in the first direction with the capped syringe supportably suspended therefrom.

As may be appreciated, the provision of a loading member and a support member that may each supportably receive a cap of a capped syringe, wherein the capped syringe is supportably suspended from the loading member and support member, provides a syringe loading and transfer arrangement that accommodates a range of syringe sizes. In that regard, the loading member and support member may be provided to supportably receive capped syringes of varying dimensions which are each capped with locating caps having a common configuration.

In some embodiments, the channel of the loading member may be downwardly angled from the first end to the second end thereof, thereby providing for automatic, gravity-induced movement of a supportably suspended, capped syringe(s) from the first end to the second end of the channel. Optionally, the downwardly angled channel may be of a helical configuration, thereby of the channel yielding compactness.

In some arrangements the channel may be of an inverted C-shaped configuration, wherein the cap of a capped syringe is received within the channel and supported by opposing spaced flanges of the channel. In turn, a barrel of the suspended capped syringe may extend downward between the flanges.

In some implementations, the channel may include a seat portion at the second end thereof to locate a capped syringe in a predetermined orientation relative to the first position of the support member. In that regard, the seat portion may be configured to supportably receive a rim portion of the cap of a capped syringe. By way of example, one or both flanges of an inverted C-shaped channel may be provided with a pair of upwardly-oriented protrusions configured to receive a portion of a downwardly oriented chevron surface of the cap of a capped syringe therebetween.

In some embodiments, the apparatus for syringe loading and transfer may further comprise a moveable arm for engagement with a cap of a capped syringe to advance the capped syringe from a supported position at the second end of the channel to the support member at the first position. In some embodiments, the arm member may be disposed for positioning in an open orientation transverse to the channel upstream from the second end thereof with the cap of a capped syringe located between the arm member and the second end of the channel. In turn, the arm member may be provided for pivotal movement from the open orientation to the closed orientation so as to engage and thereby advance a cap of a capped syringe from the second end of the channel to a support position on the support member.

In some arrangements, the apparatus may include a mount member moveable in the first direction and in a second direction along the tray, wherein the support member may be supportably interconnected to and moveable with the mount member at an elevated position relative to the tray. In that regard, the support member may be moveable relative to the mount member to facilitate release of a capped syringe supportably suspended from the support member for receipt by the tray after the support member is moved from the first position in the first direction. In that regard, the support member may be disposed to move from a support orientation to a release orientation after movement of the support member from the first position in the first direction. By way of example, the support member may be disposed for pivotal movement relative to the mount member (e.g. pivotal movement upward/downward about a horizontal axis) from the support orientation to the release orientation.

In some embodiments, to facilitate release of the capped syringe from the support member disposed in a release orientation, the apparatus may include a fixed surface located to engage, or "knock down" the support member during movement of the support member in the first direction from the first position. By way of example, the fixed surface may comprise a downward-oriented surface located to engage the support member in an upwardly-angled position during movement of the support member and thereby abruptly cause the support member to pivot downward from the release orientation to the support orientation and thereby release the capped syringe into the tray in a desired location. In conjunction with such arrangements, the support member may further comprise at least one upstanding engagement stub for engagement with a fixed surface.

In some embodiments, the arm member may be supportably interconnected to and moveable with the mount member. Further, the arm member may be moveable relative to the mount member for engagement with the cap of a capped syringe upon movement of the support member in the second direction into the first position. In that regard, the arm member may be disposed to move from an open orientation to a closed orientation, relative to the support member, during movement of the support member in the second direction into the first position. More particularly, and as noted above, the arm member may be disposed for positioning in the open orientation, transverse to the channel upstream from the second end thereof, and for pivotal movement from the open orientation to the closed orientation during movement of the support member in the second direction into the first position. For such purposes, the apparatus may further comprise a fixed surface configured and located to engage and thereby pivot the arm member from the open orientation to the closed orientation upon the movement of the support member in the second direction into the first position. In that regard, the arm member may include a cam member for camming engagement with the fixed surface during final movement of the support member in the second direction into the first position. Further, the arm member may be biased to assume the open orientation, wherein upon movement of the support member in the first direction away from the first position the cam member may disengage from the fixed surface and the arm member may automatically move to the open orientation.

Various embodiments may comprise any number of combinations of apparatus and/or method features described above and/or hereinbelow. Such combinations may include those encompassed by the following Embodiments:

1. An apparatus for syringe positioning, comprising:
a first member having an upstanding, first surface; and,
a second member having an upstanding, second surface facing said first surface of said first member, wherein said first and said second surfaces include first and second ramps, respectively, that angle upward and away from one another, wherein at least one of the first and second members is advanceable toward the other one of the first and second members, and wherein upon said advancement the first and second ramps are operable to engage, elevate and thereby locate a syringe in an axially aligned position on a predetermined axis extending between the first and second members.

2. An apparatus as recited in Embodiment 1, further comprising:
an actuator to linearly advance the first member toward the second member.

3. An apparatus as recited in Embodiment 1 or Embodiment 2, wherein said actuator comprises:

a motor having a controller to automatically terminate operation of the motor upon motor stalling.

4. An apparatus as recited in any one of Embodiments 1-3, wherein said actuator is operable to provide an output indicative of a length of a syringe located in an axially aligned position on said predetermined axis.

5. An apparatus as recited in any one of Embodiments 1-4, wherein the first member is advanceable by an actuator toward the second member and the second member is disposed in a fixed location.

6. An apparatus as recited in any one of Embodiments 1-5, wherein said first and second surfaces include first and second lip portions, respectively, that extend upward from the first and second ramps, respectively, to define first and second concave regions, respectively.

7. An apparatus as recited in any one of Embodiments 1-6, wherein said first and second ramps are at least partially defined by corresponding inclined first and second channels, respectively, extending along corresponding lengths thereof.

8. An apparatus as recited in any one of Embodiments 1-7, wherein said first surface includes a first portion having a first conical configuration centered on said predetermined axis and said second surface includes a first portion having a second conical configuration centered on said predetermined axis.

9. An apparatus as recited in any one of Embodiments 1-8, further comprising:
a tray defining a V-shaped recession that extends from the second member towards the first member, wherein said first member is advanceable by said actuator over and along the V-shaped recession towards the second member.

10. An apparatus as recited in any one of Embodiments 1-9, wherein said first and second channels have corresponding parabolic configurations that conformally adjoin the first portions of the first and second surfaces, respectively.

11. An apparatus as recited in any one of Embodiments 1-10, wherein said second member comprises:
an upwardly angled groove formed in said second member and extending along at least a portion of the second channel with a top end located within the first portion of the second member.

12. An apparatus as recited in any one of Embodiments 1-11, wherein said groove is of an elongated diamond configuration.

13. An apparatus as recited in any one of Embodiments 1-12, wherein said tray comprises:
a bottom slot extending along a length of the V-shaped recession of the tray to a base of the second member adjacent to a bottom end of said groove.

14. An apparatus as recited in any one of Embodiments 1-13, wherein the first member comprises:
a projection that extends in to and advances along at least a portion of the slot upon advancement of the first member towards the second member.

15. An apparatus as recited in any one of Embodiments 1-14, wherein the second member comprises:
an aperture located on said predetermined axis and sized to receive one of a dispensing tip and a projecting tip of a cap located on a dispensing tip of a syringe, wherein said first portion of the second surface extends about the aperture.

16. An apparatus as recited in any one of Embodiments 1-15, wherein the second member comprises:
an aperture located on said predetermined axis and sized to receive one of a dispensing tip and a projecting tip of a cap located on a dispensing tip of a syringe, wherein at least a portion of the second surface extends about the aperture.

17. An apparatus as recited in any one of Embodiments 1-16, further comprising:
a sensor for sensing the positioning of one of a dispensing tip and a projecting tip of a cap located on a dispensing tip of a syringe within said aperture, and for providing an output signal in response thereto.

18. An apparatus as recited in any one of Embodiments 1-17, wherein said output signal is indicative of the presence of one of a dispensing tip and a cap tip located on a dispensing tip of a syringe positioned at a predetermined location within the aperture.

19. An apparatus as recited in any one of Embodiments 1-18, wherein said sensor comprises:
a capacitive sensor for sensing an electrical capacitance that is dependent upon a position of one of a dispensing tip and a projecting tip of a cap located on a dispensing tip of a syringe relative to said aperture.

20. An apparatus as recited in any one of Embodiments 1-19, wherein said capacitive sensor comprises first and second conductive surfaces, and wherein said sensor further comprises:
a rod member having a first end located at said aperture and a second end located to displace at least one of the first and second conductive surfaces upon positioning of one of a dispensing tip and a projecting tip of a cap located on a dispensing tip of a syringe within said aperture.

21. An apparatus as recited in any one of Embodiments 1-20, wherein said at least one of the first and second conductive surfaces is defined by a spring member located to bias said rod member so that the first end thereof is at said predetermined location in said aperture prior to said positioning of one of a dispensing tip and a projecting tip of a cap located on a dispensing tip of a syringe within said aperture.

22. An apparatus as recited in any one of Embodiments 1-21, wherein said output signal is further indicative of the presence of one of a dispensing tip and a cap tip located on a dispensing tip of a syringe positioned at a location different from said predetermined location within the aperture.

23. An apparatus as recited in any one of Embodiments 1-22, wherein said actuator is controllable to automatically retract the first member away from the second member when said output signal is indicative of the presence of one of a dispensing tip and a cap tip located on a dispensing tip of a syringe positioned at a location different from said predetermined location within the aperture.

24. An apparatus as recited in any one of Embodiments 1-23, wherein said second surface includes a stop portion configured to conformally engage a surface of a cap located on a dispensing tip of a syringe and having a projecting tip positioned at the predetermined location within said aperture.

25. An apparatus as recited in any one of Embodiments 1-24, wherein said first surface includes a first portion having a first conical configuration centered on said predetermined axis and said second surface includes a first portion having a second conical configuration centered on said predetermined axis, and wherein said first portion includes said stop portion centered on said predetermined axis.

26. An apparatus as recited in any one of Embodiments 1-25, further comprising:
a tray for supportably receiving a syringe; and,
a mount member moveable along said tray in a first direction from a retracted position and in a second direction toward the retracted position, said first member being supportably interconnected to and moveable with the mount member, wherein during movement of the mount member in said first direction from the retracted position the first member advances toward the second member and is disposed to pass through a first region of the tray to engage and thereby advance a syringe from the first region in to a second region of the tray within which the first member and second member are operable to engage, elevate and thereby locate the syringe on said predetermined axis, and wherein during movement of the mount member in the second direction toward the retracted position the first member retracts away from the second member and is disposed to bypass the first region.

27. An apparatus as recited in any one of Embodiments 1-26, wherein the first member is moveable relative to the mount member and disposed to move from a first orientation to a second orientation for said bypass of the first region during movement of the mount member in the second direction.

28. An apparatus as recited in any one of Embodiments 1-27, further comprising:
a guide member disposed to guide said first member in said second orientation for said bypass of the first region during movement of the mount member in the second direction.

29. An apparatus as recited in any one of Embodiments 1-28, wherein the first member is disposed to move to the first orientation from the second orientation after said bypass of the first region during movement of the mount member in the second direction.

30. An apparatus as recited in any one of Embodiments s 1-29, wherein said guide member is disposed to guide said first member to the first orientation from the second orientation after said bypass of the first region during movement of the mount member in the second direction.

31. An apparatus as recited in any one of Embodiments 1-30, wherein the first member is disposed in said first orientation for said passage through the first region and in to the second region during movement of the mount member in the first direction.

32. An apparatus as recited in any one of Embodiments 1-31, wherein said guide member is disposed to guide said first member in said first orientation for said passage through the first region and in to the second region during movement of the mount member in the first direction.

33. An apparatus as recited in any one of Embodiments 1-32, wherein the first member is pivotably interconnected to the mount member and disposed to pivot from the first orientation to the second orientation for said bypass of the first region during movement of the mount member in the second direction, and to pivot to the first orientation from the second orientation after said bypass of said first region during movement of the mount member in the second direction.

34. An apparatus as recited in any one of Embodiments 1-33, wherein said guide member is disposed to guide the first member in the second orientation for said bypass of the first region during movement of the mount member in the second direction, and to guide said pivotal movement of the first member to the first orientation from the second orientation after said bypass of said first region during movement of the mount member in the second direction.

35. An apparatus as recited in any one of Embodiments 1-34, wherein said first member is pivotably interconnected to the mount member at a pivot axis elevated relative to the tray, and wherein said first member is pivoted downward in said first orientation and upward in said second orientation.

36. An apparatus as recited in any one of Embodiments 1-35, further comprising:
a carrier member supportably and pivotably interconnected to the mount member at said pivot axis, wherein the first member is interconnected in fixed relation to the pivot member for pivotable co-movement therewith.

37. An apparatus as recited in any one of Embodiments 1-36, wherein said carrier member comprises at least one guide follower, and wherein said guide member comprises:
a first guide track to interface with said at least one guide follower to guide said first member in said first orientation for said passage through the first region and in to the second region during movement of the mount member in the first direction; and,
a second guide track to interface with said at least one guide follower to guide said pivotal movement of the first member in the second orientation for said bypass of the first region during movement of the mount member in the second direction, and to guide said pivotal movement of the first member to the first orientation from the second orientation after said bypass of said first region during movement of the mount member in the second direction.

38. An apparatus as recited in any one of Embodiments 1-37, further comprising:
a diverter member to divert said at least one guide follower to interface with said second guide track during movement of the mount member from the second region in the second direction toward the retracted position.

39. An apparatus as recited in any one of Embodiments 1-38, wherein said diverter member is pivotable relative to said guide member and disposed to pivot from a first position to a second position during engagement with said at least one guide follower during movement of the mount member in said first direction from the retracted position, and to maintain said first position during engagement with said at least one guide follower during movement of the mount member from the second region in the second direction toward the retracted position.

40. An apparatus as recited in any one of Embodiments 1-39, further comprising:
a support member for supportably receiving a syringe at a first position of the support member, wherein said support member is interconnected to said mount member for co-movement therewith from said first position in said first direction to transfer the syringe to said first region of said tray.

41. An apparatus as recited in any one of Embodiments 1-40, further comprising:
a loading member for supportably receiving and successively presenting different ones of a plurality of syringes for receipt by the support member.

42. An apparatus as recited in any one of Embodiments 1-41, further comprising:
a moveable arm member to advance a syringe from the loading member to the support member.

43. An apparatus as recited in any one of Embodiments 1-42, further comprising:
an actuator to linearly move said mount member in said first direction and said second direction.

44. An apparatus as recited in any one of Embodiments 1-43, wherein said actuator comprises:
a motor having a controller to automatically control operation of the motor for movement of said mount member in the second direction to locate said support member at the first position.

45. A method for syringe positioning, comprising:
advancing at least one of a first member and a second member toward the other one, wherein the first and second members have upstanding, first and second surfaces, respectively, facing one another and including first and second ramps, respectively, that angle upward and away from one another, and wherein a syringe is located between the first and second surfaces; and, engaging first and second ends of said syringe with said first and second ramps, respectively, during said advancing to elevate and thereby locate the syringe in an axially aligned position on a predetermined axis extending between the first and second members.

46. A method as recited in Embodiment 45, wherein said advancing comprises:

utilizing an actuator to linearly advance the first member toward the second member.

47. A method as recited in Embodiment 45 or Embodiment 46, wherein said actuator includes a motor having a controller to automatically control a speed of the motor, and wherein the utilizing comprises:

operating the motor to provide a mechanical output to advance the first member toward the second member; and, terminating automatically operation of the motor when the motor stalls.

48. A method as recited in any one of Embodiments 45-47, further comprising:

providing an output indicative of a length of the syringe upon positioning of the syringe in the axially aligned position on the predetermined axis.

49. A method as recited in any one of Embodiments 45-48, wherein said output is provided by said actuator and is further indicative of a position of the first member relative to a predetermined reference location.

50. A method as recited in any one of Embodiments 45-49, wherein said first and second surfaces include first and second lip portions, respectively, that extend upward from the first and second ramps, respectively, to define first and second concave regions, respectively.

51. A method as recited in any one of Embodiments 45-50, wherein said first and second ramps are at least partially defined by corresponding inclined first and second channels, respectively, extending along corresponding lengths thereof, and wherein said engaging comprises:

utilizing the first and second channels to direct said first and second ends of the syringe towards the axially aligned position on the predetermined axis.

52. A method as recited in any one of Embodiments 45-51, wherein said first surface includes a first portion having a first conical configuration centered on said predetermined axis and said second surface includes a first portion having a second conical configuration centered on said predetermined axis, and wherein said engaging further comprise:

employing the conical first portions to center the first and second ends of said syringe on the predetermined axis.

53. A method as recited in any one of Embodiments 45-52, further comprising:

supporting the syringe in a tray defining a V-shaped recession that extends from the second member towards the first member, wherein the first member advances over and along the V-shaped recession towards the second member during said advancing.

54. A method as recited in any one of Embodiments 45-53, wherein the second member comprises an aperture located on said predetermined axis and sized to receive one of a dispensing tip and a projecting tip of a cap located on a dispensing tip of a syringe, and further comprising:

sensing the positioning of one of a dispensing top and a projecting tip of a cap located on a dispensing tip of a syringe within said aperture, and providing an output signal in response thereto.

55. A method as recited in Embodiments 54, wherein said output signal is indicative of the presence of one of a dispensing tip and a cap tip located on a dispensing tip of a syringe positioned at a predetermined location within the aperture.

56. A method as recited in any one of Embodiments 45-55, wherein said sensor comprises:

a capacitive sensor for sensing an electrical capacitance that is dependent upon a position of one of a dispensing tip and a projecting tip of a cap located on a dispensing tip of a syringe relative to said aperture, wherein said capacitive sensor comprises first and second conductive surfaces.

57. A method as recited in any one of Embodiments 45-56, wherein said sensor further comprises a rod member having a first end located at said aperture and a second end located to engage at least one of the first and second conductive surfaces, and further comprising:

displacing at least one of the first and second conductive surfaces by the second end of the rod member upon positioning of one of a dispensing tip and a projecting tip of a cap located on a dispensing tip of syringe within said aperture.

58. A method as recited in any one of Embodiments 45-57, wherein the first member is supportably interconnected to a mount member that is moveable along said tray in a first direction from a retracted position toward the second member and in a second direction toward the retracted position, and wherein said advancing comprises:

first moving said mount member in said first direction from the retracted position, wherein the first member is disposed to pass through a first region of the tray to engage and thereby advance a syringe from the first region in to a second region of the tray within which the first member and second member engage, elevate and thereby locate the syringe on said predetermined axis.

59. A method as recited in any one of Embodiments 45-58, further comprising:

second moving said mount member in said second direction toward the retracted position, wherein the first member is disposed to bypass the first region relative to the tray.

60. A method as recited in any one of Embodiments 45-59, wherein the first member is moveable relative to the mount member and disposed in a first orientation during said first moving step, and further comprising:

moving said first member from said first orientation to a second orientation during the said second moving for said bypass of the first region.

61. A method as recited in any one of Embodiments 45-60, wherein said moving comprises:

guiding said first member from said first orientation to said second orientation for said bypass of the first region.

62. A method as recited in any one of Embodiments 45-61, wherein said moving further comprises:

moving said first member from said second orientation to said first orientation after said bypass of the first region.

63. A method as recited in any one of Embodiments 45-62, wherein said guiding further comprises:

guiding said first member from said second orientation to said first orientation after said bypass of the first region.

64. A method as recited in any one of Embodiments 45-63, wherein said moving comprises:

pivoting said first member from the first orientation to the second orientation.

65. An apparatus for syringe loading and transfer, comprising:

a loading member having a channel for receiving a cap located on a dispensing tip of a capped syringe at a first end of the channel, wherein the capped syringe is supportably suspended from the channel;

a support member for receiving the cap of the capped syringe from the loading member at a first position adjacent to a second end of the channel, wherein said support member is moveable to transfer the capped syringe from said first position in a first direction with said capped syringe supportably suspended therefrom; and, a tray for supportably receiving said capped syringe from the support member and supporting the capped syringe in a reclined position after said support member is moved from said first position in said first direction.

66. An apparatus as recited in Embodiment 65, wherein said channel is downwardly angled from said first end to said second end thereof.

67. An apparatus as recited in Embodiment 65 or Embodiment 66, wherein said channel is of a helical configuration.

68. An apparatus as recited in any one of Embodiments 65-67, wherein said channel is of an inverted C-shaped configuration and comprises:

a seat portion at said second end to locate said capped syringe at a predetermined location relative to the first position of the support member.

69. An apparatus as recited in any one of Embodiments 65-68, further comprising:

a moveable arm member for engagement with the cap of said capped syringe to advance the capped syringe from the second end of the channel to the support member at said first position.

70. An apparatus as recited in any one of Embodiments 65-69, further comprising:

a mount member moveable in said first direction and in a second direction along said tray, wherein said support member is supportably interconnected to and moveable with said mount member at an elevated position relative to the tray.

71. An apparatus as recited in any one of Embodiments 65-70, wherein said support member is moveable relative to said mount member to release the capped syringe from the support member for receipt by said tray after said support member is moved from the first position in said first direction.

72. An apparatus as recited in any one of Embodiments 65-71, wherein the support member is disposed to move from a support orientation to a release orientation after movement of the support member from the first position in said first direction.

73. An apparatus as recited in any one of Embodiments 65-72, wherein said support member is disposed for pivotal movement from said support orientation to said release orientation.

74. An apparatus as recited in any one of Embodiments 65-73, further comprising:

a fixed surface located to engage said support member to release said capped syringe after movement of the support member from the first position.

75. An apparatus as recited in any one of Embodiments 65-74, wherein said support member comprises:

at least one upstanding engagement stub for engagement with said fixed surface.

76. An apparatus as recited in any one of Embodiments 65-75, wherein said arm member is supportably interconnected to and moveable with said mount member.

77. An apparatus as recited in any one of Embodiments 65-76, wherein said arm member is moveable relative to said mount member for said engagement with the cap of said capped syringe upon movement of the support member in said second direction into said first position.

78. An apparatus as recited in any one of Embodiments 65-77, wherein said arm member is disposed to move from an open orientation to a closed orientation, relative to said support member, upon movement of said support member in said second direction into said first position.

79. An apparatus as recited in any one of Embodiments 65-78, wherein said arm member is disposed for positioning in said open orientation transverse to said channel upstream from the second end thereof, and for pivotal movement from said open orientation to said closed orientation upon said movement of said support member in said second direction into said first position.

80. An apparatus as recited in any one of Embodiments 65-79, wherein said arm member is biased to assume said open orientation, and further comprising:

a fixed surface configured to pivot said arm member from said open orientation to said closed orientation upon said movement of said support member in said second direction into said first position.

81. An apparatus as recited in any one of Embodiments 65-80, wherein said cam member comprises:

a cam member for camming engagement with said fixed surface.

82. An apparatus as recited in any one of Embodiments 65-81, further comprising:

an actuator to linearly move said mount member in said first direction and said second direction.

83. An apparatus as recited in any one of Embodiments 65-82, wherein said actuator comprises:

a motor having a controller to automatically control operation of the motor for movement of said mount member in the second direction to locate said support member at the first position.

84. An apparatus as recited in any one of Embodiments 65-83, further comprising:

a first member supportably interconnected to and moveable with said mount member, and having an upstanding, first surface; and, a second member disposed at a fixed location and having an upstanding, second surface facing said first surface of said first member, wherein said first and second surfaces include first and second ramps, respectively, that angle upward and away from one another, and wherein upon movement of said mount member in said first direction the first and second ramps are operable to engage another capped syringe supported in a reclined orientation in said tray, and to elevate and thereby locate said another capped syringe in an axially aligned position on a predetermined axis extending between the first and second members.

85. An apparatus as recited in any one of Embodiments 1-44 or Embodiments 65-84, for performing a method as recited in any one of Embodiments 45-64.

Additional features and advantages of the present invention will become apparent upon consideration of the description that follows.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular application(s) or use(s) of the present invention.

Figure 1:
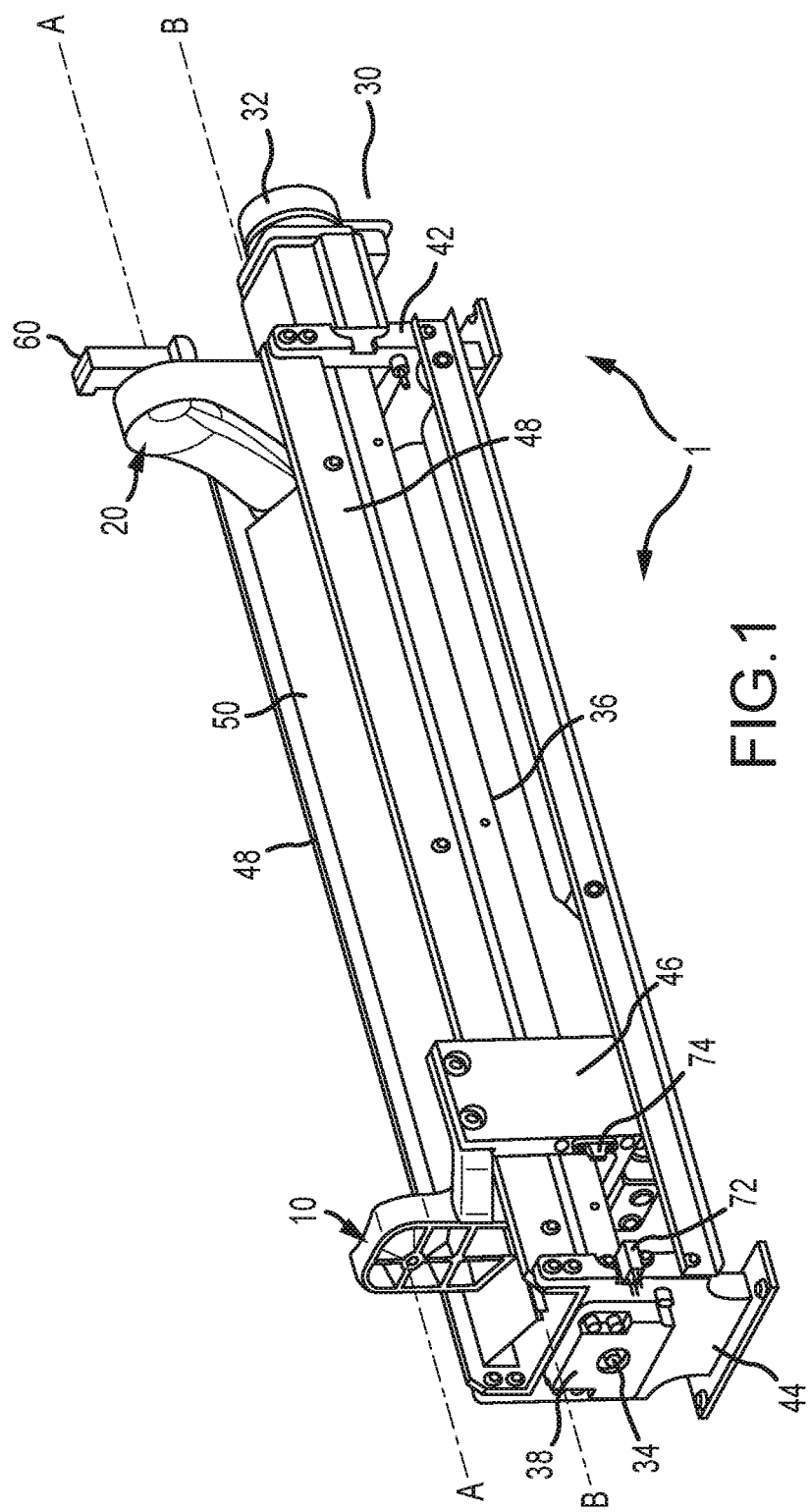
FIG. 1 is a perspective view of one embodiment of a syringe positioning apparatus.

One embodiment of a syringe positioning apparatus (1) is shown in FIG. 1 and includes a first member (10) and a second member (20) provided for relative movement to locate a syringe (e.g. capped or uncapped) in an axially aligned position on a predetermined axis AA extending therebetween. In particular, in the illustrated embodiment the first member (10) is linearly advanceable toward and retractable away from the second member (20) via an actuator (30) operatively interconnected to the first member (10). The actuator (30) may be provided to advance the first member (10) so as to locate a syringe between the first and second members (10), (20), in an axially aligned position on the predetermined axis AA, with an end of the syringe engaged with the second member (20) at a predetermined or determinable location, as will be further described herein below.

The actuator (30) may include an electric motor (32) having a controller to automatically control a speed of the motor (30). In turn, the motor may be operated to provide a mechanical output to advance the first member (10) towards the second member (20) until the motor stalls, whereupon the controller automatically terminates operation of the motor (32) and the actuator maintains the first member at a corresponding advanced position. The motor controller may be provided so that, upon advancement of first member toward the second member a syringe may be supportably engaged and restrainably located in an axially aligned position on the predetermined axis AA between the first member (10) and second member (20), while maintaining an axial compression force applied to the syringe within a predetermined range (e.g. within a range of about 5N to about 20N). By way of example, motor (32) may comprise a brushless DC motor having a controller that controls the motor (32) utilizing pulse width modulation control.

The motor (32) may be operable to provide an output indicative of a length of a syringe located between the first and second members (10), (20), in an axially aligned position on the predetermined axis AA. In one approach, the output may be indicative of a distance of travel of the first member (10) from a predetermined home position to a position at which a syringe is positioned between the first member (10) and second member (20) in an axially aligned position on the predetermined axis AA, with an end of the syringe located at a predetermined or determinable position. For such purposes, a sensor (72) may be disposed at a fixed location adjacent to the predetermined home position of the first member (10), and a sensor tag (74) may be interconnected to the first member (10) for co-movement therewith. In FIG. 1, the first member (10) is shown slightly advanced from the predetermined home position. The sensor (72) may be provided to sense whether and/or when the sensor tag (74) is located at a location that corresponds with positioning of the first member (10) at the predetermined home position, and to provide an output signal to motor (32) in response thereto.

The motor (32) may comprise a BLDC-type motor. In turn, prior to a given syringe positioning procedure, the first member (10) may be positioned at the predetermined home position and sensor (72) may provide an output signal to the motor (32). To achieve syringe positioning, the motor (32) may operate to advance the first member (10) to an advanced position at which a syringe is positioned between the first and second members (10), (20), at an axially aligned position on the predetermined axis AA, with an end of the syringe located at a predetermined or determinable position. In conjunction therewith, the motor (32) may comprise Hall effect sensors to provide an output that is indicative of a motor rotation so that a counted number of the sensor pulses are associated with positioning the first member from the predetermined home position to the advanced position. As may be appreciated, each sensor pulse may correspond with a predetermined displacement distance of first member (10). In turn, the output of motor (32) sensors is indicative of the distance traveled by first member (10), and in turn, such output is indicative of the length of the positioned syringe.

In the illustrated embodiment, actuator (30) may be an electro-mechanical actuator that includes the electric motor (32) supportably interconnected to a first support member (42), and a linear actuator (34). The linear actuator (34) may be supportably and operatively interconnected at a first end to electric motor (32) and may extend through a housing (36) to a second end that may be supportably interconnected to a second support member (44). In some implementations, the first end of the linear actuator (34) may be mechanically interconnected to a rotatable output of electric motor (32) and the second end of the linear actuator (34) may be supported for rotation relative to a journal plate (38) at the second support member (44). In such implementations, the linear actuator (34) may comprise a lead screw/traveling nut arrangement, wherein the first member (10) is interconnected via a mount member (46) to the traveling nut for co-movement therewith. In turn, upon driven rotation of the linear actuator (34) by the rotatable output shaft of electric motor (32) the traveling nut and interconnected first member (10) may be selectively advanced toward and retracted away from the second member (20). As may be appreciated, the linear actuator (34) may be provided to maintain first member (10) in an advanced position at which operation of the motor (32) is automatically terminated, as described above, with a syringe located in an axially aligned position on the predetermined axis AA, with an end of the syringe engaged with the second member (20) at a predetermined or determinable location.

The syringe positioning apparatus (1) may include a tray (50) that extends away from second member (20) towards and under the first member (10), wherein the first member (10) is advanceable over and along the tray (50). The tray (50) may define a V-shaped recession having a longitudinal axis BB that extends along a length of the tray (50). In that regard, the tray (50) may be provided so that the longitudinal axis BB is parallel to the predetermined axis AA. As will be further described, the V-shaped recession of tray (50) may support a syringe received by tray (50) in substantially aligned relation with longitudinal axis BB.

In some implementations, the tray (50) and the second member (20) may be supported by a frame (48) that is supportably interconnected at first and second ends to first support member (42) and second support member (44), respectively. In that regard, the second member (20), tray (50), and motor (32) may be disposed in fixed relation to one another via the first and second support members (42), (44) and frame (48).

As indicated, the first member (10) and second member (20) may be provided to locate a syringe in an axially aligned position on the predetermined axis AA extending between the first member (10) and second member (20). In that regard, when first member (10) is advanced toward second member (20), a first end of a reclined syringe supported by tray (50) may be engaged by the first member (10) to slidably advance the syringe along the V-shaped recession of tray (50), causing a second end of the syringe to engage the second support member (20). In turn, upon further advancement of the first member (10), the first and second ends of the syringe may slidably engage the first and second members (10), (20), respectively, for positioning into an axially aligned position on the predetermined axis AA, as shown in the example of FIG. 2.

Figure 2:
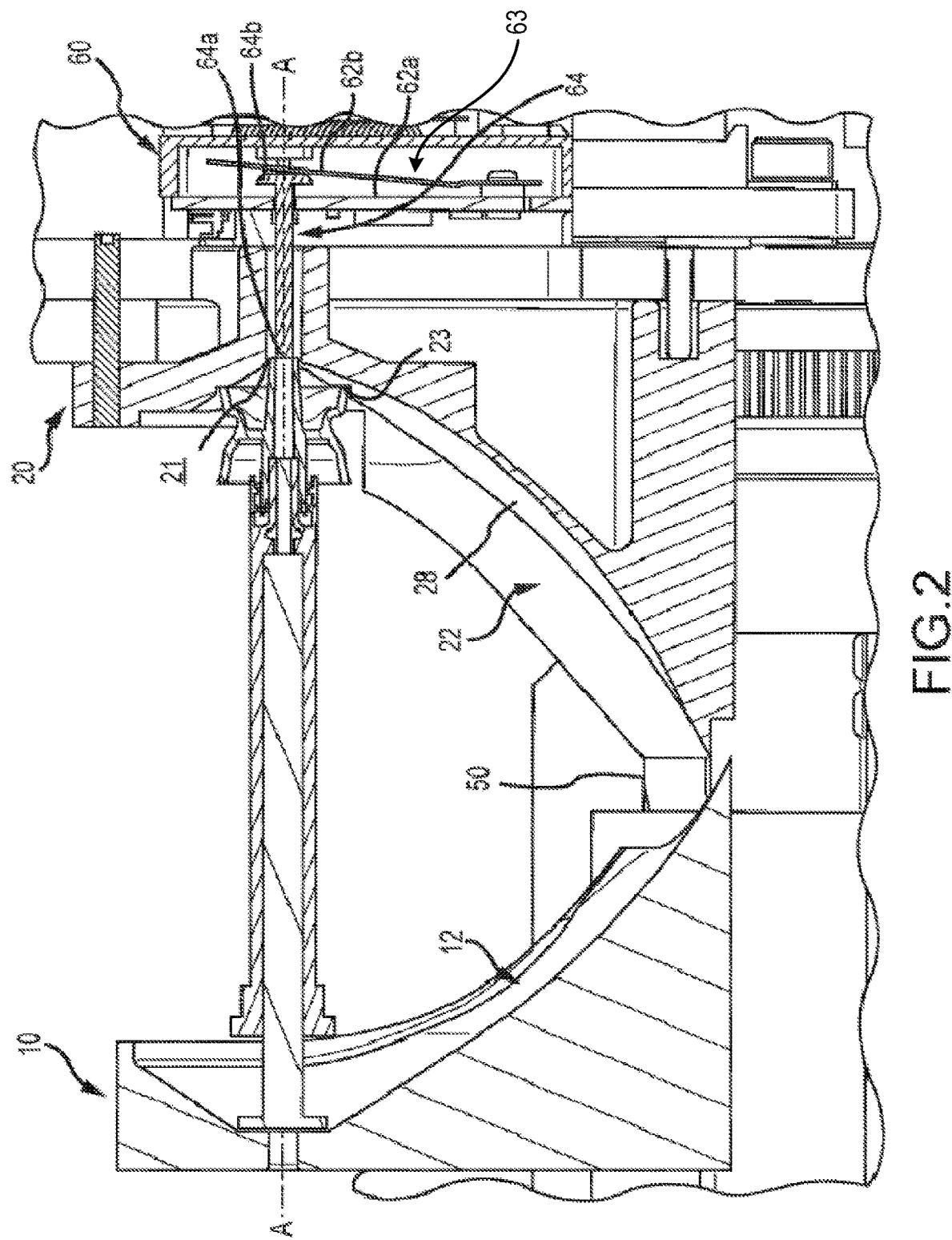
FIG. 2 is a side cross-sectional view of the syringe positioning apparatus embodiment of FIG. 1, illustrating an example of a syringe axially aligned on a predetermined axis AA between first and second members.

With reference to FIG. 2, the first member (10) may include an upstanding first surface (12), and the second member (20) may include an upstanding second surface (22) facing the first surface of the first member (10), wherein the first and second surfaces (12), (22) may be smoothly contoured to include first and second ramps, respectively, that angle upward and away from one another. As such, upon advancement of the first member (10) toward the second member (20), the first and second ramps are operable to slidably engage a syringe located in tray (50), and progressively elevate the syringe from a reclined position in tray (50) to an axially aligned position on the predetermined axis AA extending between the first member (10) and second member (20).

As will be appreciated, the first ramp of the first member (10) and the second ramp of the second member (20) may each have a variety of different configurations, each of which facilitates sliding engagement of an end of a syringe up an inclined surface so as to reach the predetermined axis AA. In contemplated embodiments, the first and second ramps may each angle upward within a range of about 26.8° to 57.1° relative to common reference plane (e.g. a horizontal plane).

The first and second surfaces (12), (22) of the first and second members (10), (20), respectively, may be provided to have relatively low coefficients of friction, thereby facilitating sliding engagement with opposing ends of a syringe. For example, the first and second surfaces (12), (22) may be polished or finished (e.g. via PTFE (polytetrafluoroethylene) infused anodization) to provide a slippery surface. Further, the first and second members (10), (20) may comprise materials to yield a relatively low coefficient of friction to facilitate sliding of the opposing ends of a syringe.

As illustrated in FIG. 2, the first second surfaces (12), (22) of the first and second members (10), (20), respectively, may further include limiting portions that extend upward from the first and second ramps, respectively, to define first and second concave regions. Such first and second concave regions may function to limit travel of the ends of a syringe, thereby facilitating syringe positioning on the predetermined axis AA.

In the example shown in FIG. 2, the illustrated syringe includes barrel, a plunger extending in to an open end of the barrel, and a cap disposed on a dispensing tip that extends from the barrel. In such example, a first end of the syringe comprises a button provided at an end of the plunger, and a second end of the syringe comprises the cap. As shown FIG. 2, the cap may be a locating cap having a projecting tip positioned in an aperture (21) of the second member, as will be further described hereinbelow. In another example, the syringe positioning apparatus (1) may be used to position a syringe that does not include a cap on a dispensing tip thereof.

Figure 3A:
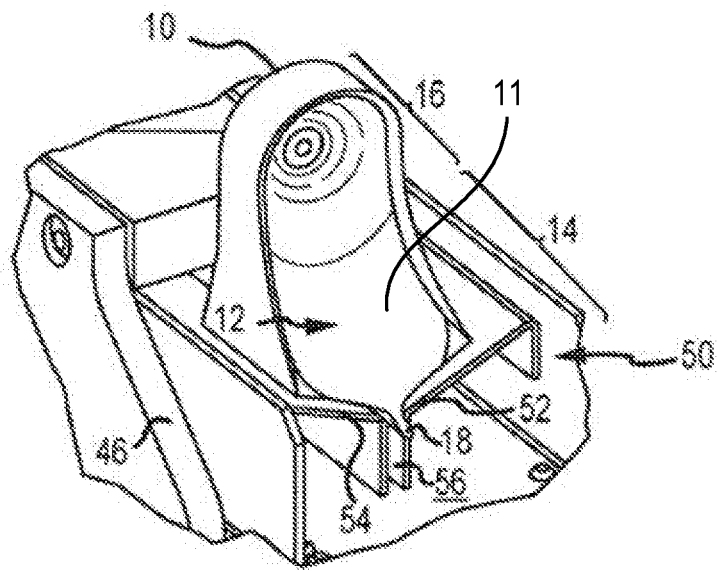
FIG. 3A is a perspective view of a first member of the syringe positioning apparatus embodiment of FIG. 1.
Figure 3B:
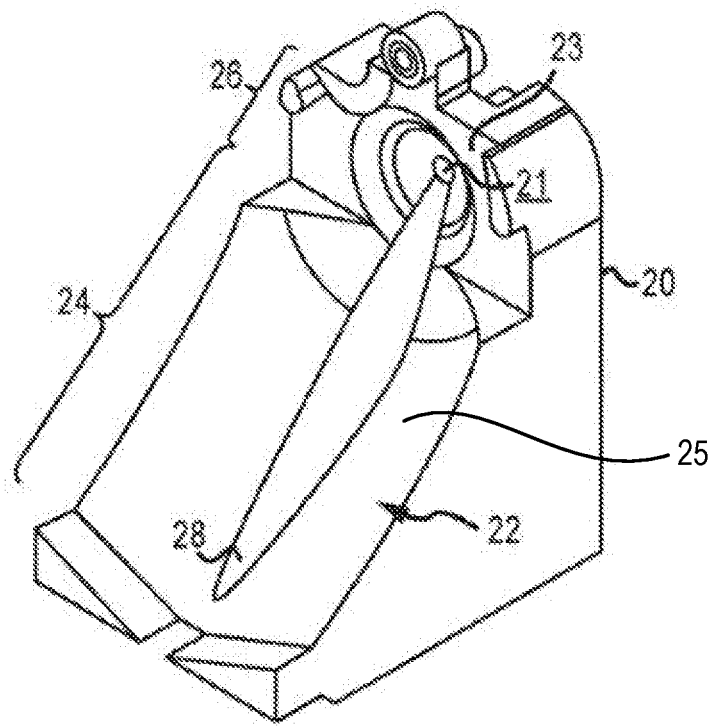
FIG. 3B is a perspective view of a second member of the syringe positioning apparatus embodiment of FIG. 1.

Reference is now made to FIGS. 3A and 3B. As shown in FIG. 3A, the first member (10) may include a first surface (12) having a first ramp (11) at least partially defined by an inclined first channel (14) extending along a length thereof. Similarly, as shown in FIG. 3B, the second member (20) may include a second surface (22) having a second ramp (25) at least partially defined by an inclined second channel (24) extending along a length thereof. The first and second channels (14), (24) may each be oriented to direct ends of a syringe towards an axially aligned position on the predetermined axis AA. As illustrated in FIGS. 3A and 3B, the first channel (14) and second channel (24) may have trough-like configurations. In that regard, the first channel (14) and second channel (24) may comprise smooth, arcuate, concave surfaces conducive to sliding engagement by an end of a syringe relative thereto.

With further reference to FIG. 3A, the first surface (12) of the first member (10) may include a first portion (16) having a first conical configuration centered on the predetermined axis AA. Similarly, as shown in FIG. 3B, the second surface (22) of the second member (20) may include a first portion (26) having a second conical configuration centered on the predetermined axis AA. As may be appreciated, the conical first portions (16), (26) facilitate axially aligned positioning of a syringe on the predetermined axis AA. In various arrangements, the first and second conical configurations may be the same or different. As further illustrated in FIGS. 3A and 3B, the first channel (14) and the second channel (24) may have parabolic configurations that conformally adjoin the conical first portions (16), (26) of the first and second surfaces (12), (22) of the first and second members (10), (20), respectively.

As shown in FIG. 3B, the second member (22) may include in an upwardly angled groove (28) extending within and along at least a portion of the second channel (24) with a top end located within the first portion (26) of the second member (20). As illustrated, the groove (28) may comprise a smooth, arcuate, concave surface. The groove (28) may be provided as a further feature to direct an end of a syringe in an axially elongated positioned on the predetermined axis AA. In particular, when a locating cap is provided at an end of a syringe (e.g. as illustrated in FIG. 2), groove (28) may be provided so that a peripheral rim of the locating cap may slidably engage and travel upward and along opposing side edges of the groove in a rail-like manner. For such purposes, groove (28) may be of an elongated, diamond configuration.

With further reference to FIG. 3A, tray (50) may be defined by first and second tray members (52), (54) oriented to define the V-shaped recession of tray (50). Further, the first and second tray members (52), (54) may be spaced at the bottom of the recession to define a slot (56) therebetween that extends along a length of the tray (50) As illustrated in FIG. 3A, the first member (10) may include a projection (18), that extends downward at a bottom end of the first channel (14) and into the slot (56) of the tray (50). The inclusion of projection (18) facilitates the advancement of smaller syringes within tray (50) and into engagement with the second member (20) upon advancement of the first member (10). In the later regard, and as shown in FIG. 3B, the second member (20) may include a recess located at the base of the second channel (24) to receive the projection (18) of the first member (10), thereby facilitating the positioning of smaller syringes.

As noted above and shown in FIGS. 2 and 3B, the second member (20) may include an aperture (21) that is located on the predetermined axis AA. The aperture (21) is sized to receive an end of a syringe, and in particular one of a dispensing tip of a syringe and a projecting tip of a locating tap located on a dispensing tip of a syringe (e.g. as shown in FIG. 2). As illustrated, the aperture (21) may be provided within the conical first portion (26) of the second surface (22). Further, groove (28) may be provided so that the top end thereof adjoins the aperture (21).

The second surface (22) of the second member (20) may further include a stop portion (23) configured to engage an end of a syringe at a predetermined location upon positioning of the syringe between the first and second members (10), (20), in an axially aligned position on the predetermined axis AA. In one approach, the stop portion (23) may be of an annular configuration that corresponds with an annular surface of a locating cap that extends about at least a portion of a projecting tip of the locating cap, as shown in FIG. 2.

Figure 4A:
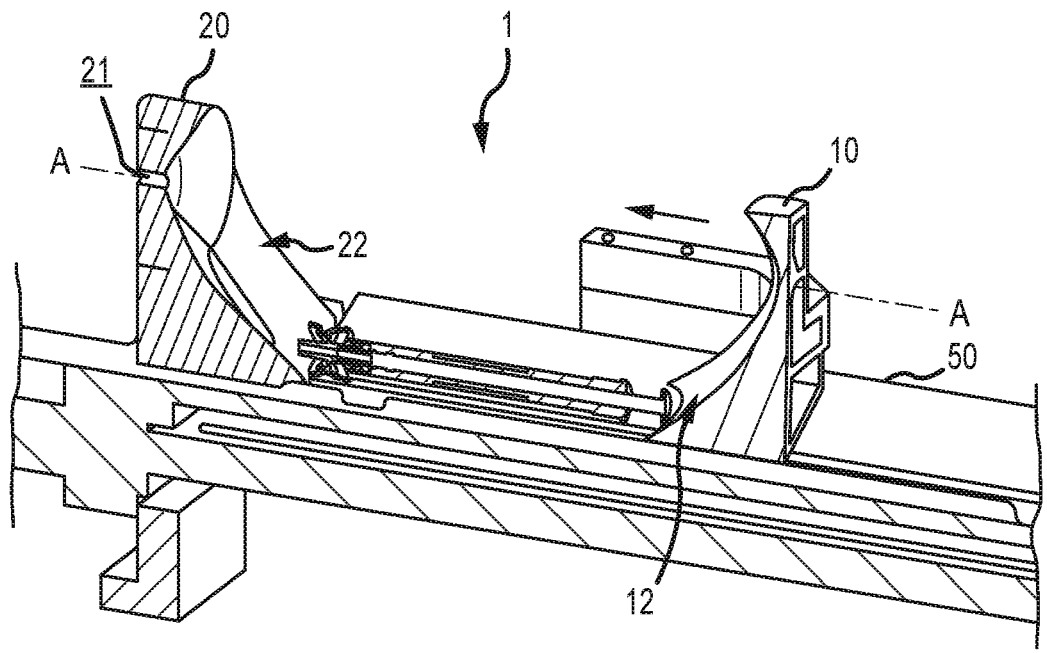
FIGS. 4A, 4B, 4C and 4D are side cross-sectional views of the syringe positioning apparatus embodiment of FIG. 1, illustrating an example of a syringe at progressive stages of positioning to an axially aligned position on a predetermined axis AA.

Reference is now made to FIGS. 4A, 4B, 4C, and 4D, which illustrate an example of a syringe at progressive stages of positioning by syringe positioning apparatus (1). Prior to the initiation of syringe positioning, the first member (10) may be located at a predetermined home position, as described above, and a syringe may be located within the recession of the tray (50). In turn, the actuator may be actuated (e.g. via operation of motor (32)) to advance the first member (10) towards the second member (20) as shown in FIG. 4A.

By way of example, the syringe may be located in the tray (50) either manually or in an automated manner. In any case, the syringe may be located so that a first end defined by a plunger button faces first member (10), and so that a second end defined by a syringe dispensing tip or a cap located on a syringe dispensing tip faces second member (20). In the illustrated example, the second end comprises a locating cap disposed on a dispensing tip of a syringe.

Figure 4B:
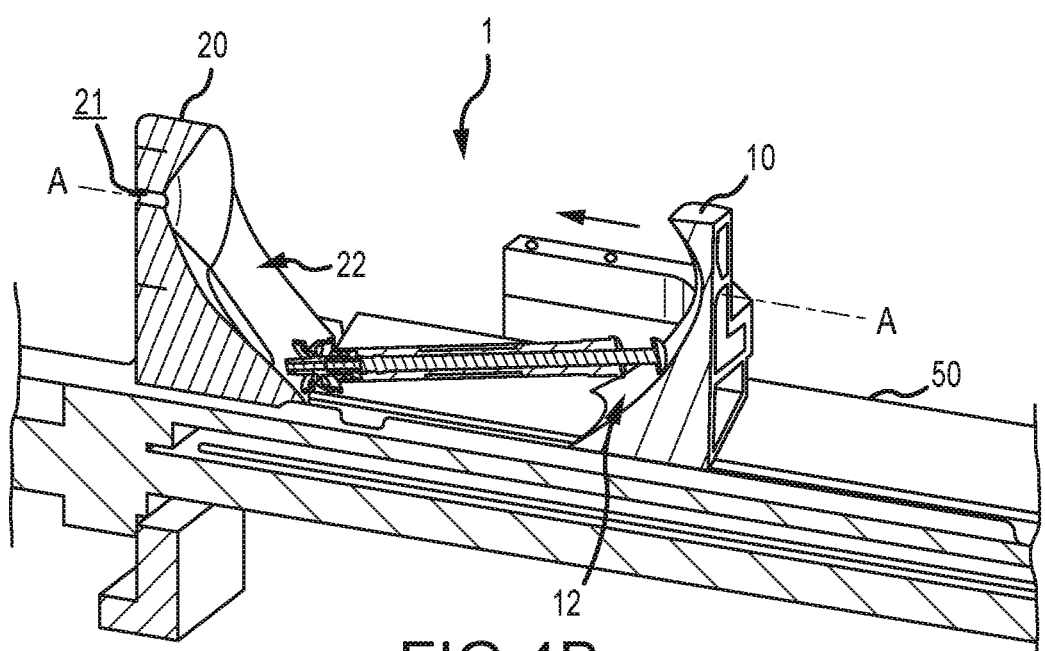
Figure 4C:
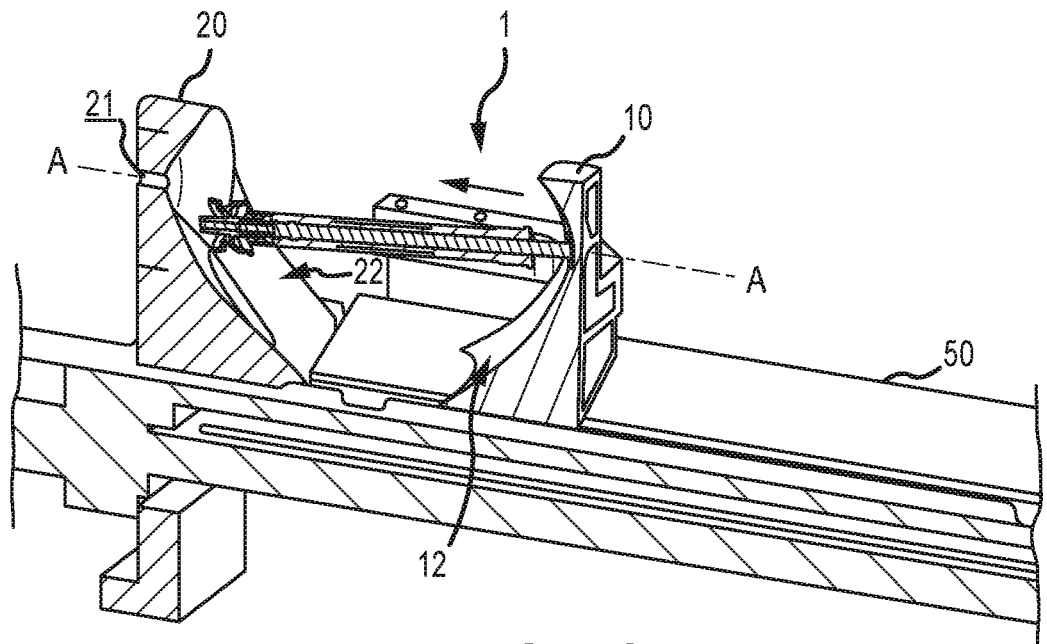
Figure 4D:
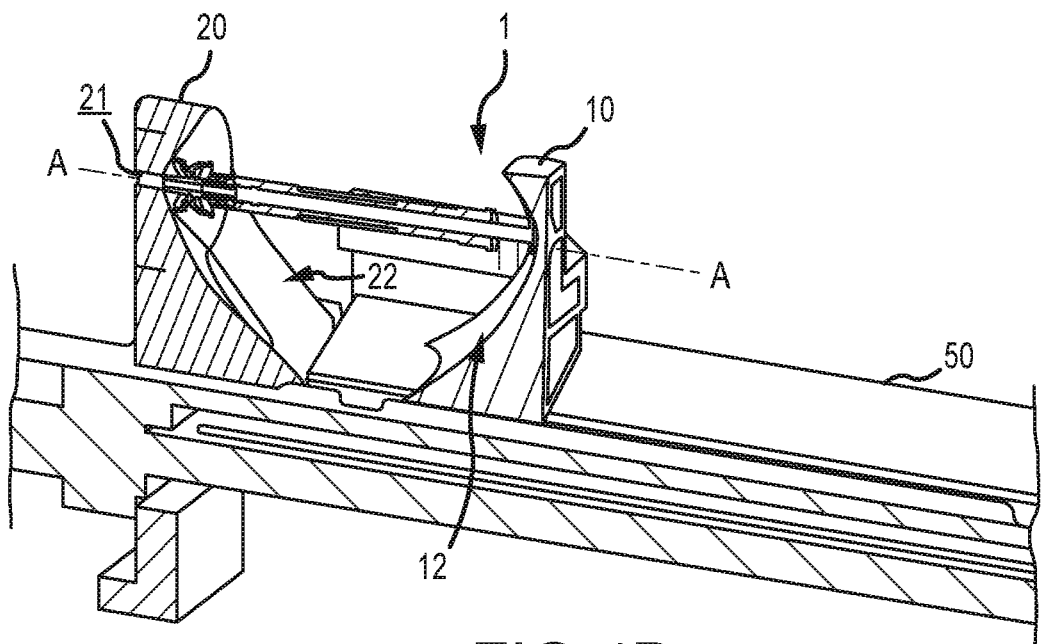

As shown in FIG. 4B, the actuator (30) may continue to advance the first member (10) towards the second member (20) so as to engage the first end of the syringe and slidably advance the syringe along the tray (50) until the second end of the syringe engages second member (20). Next, as shown in FIG. 4C, the actuator (30) may continue to advance the first member (10) towards the second member (20), thereby causing the first and second ends of the syringe to slidably advance up the first ramp of first surface (12) and second ramp of second surface (22), respectively, of the first member (10) and second member (20), respectively. As shown in FIG. 4D, the first member (10) may be further advanced toward the second member (20) until the syringe is restrainably and supportably located between the first and second members (10), (20), in an axially aligned position on the predetermined axis AA, with an end of the syringe engaged with the second member (20) at a predetermined or determinable location.

Further in that regard, in some embodiments the syringe positioning apparatus (1) may be provided with additional features to confirm positioning of an end of a syringe at a predetermined location. In particular, and with further reference to FIG. 2, the syringe positioning apparatus (1) may include a sensor (60) for sensing the positioning of one of a syringe dispensing tip and a projecting tip of locating cap located on a syringe dispensing tip, when the tip is located within the aperture (21) of the second member (20). In the example of FIG. 2, a projecting tip of a locating cap is located in the aperture (21) at a predetermined location. The sensor (60) may be provided to provide an output signal in response to the positioning of one of a syringe dispensing tip and a projecting tip of locating cap located on a syringe dispensing within the aperture (21). More particularly, the output signal may be indicative of the presence of one of a syringe dispensing tip and a projecting tip of locating cap located on a syringe dispensing tip, when such tip is positioned at the predetermined location within the aperture (21) of the second member (20), as shown in FIG. 2.

Figure 5:
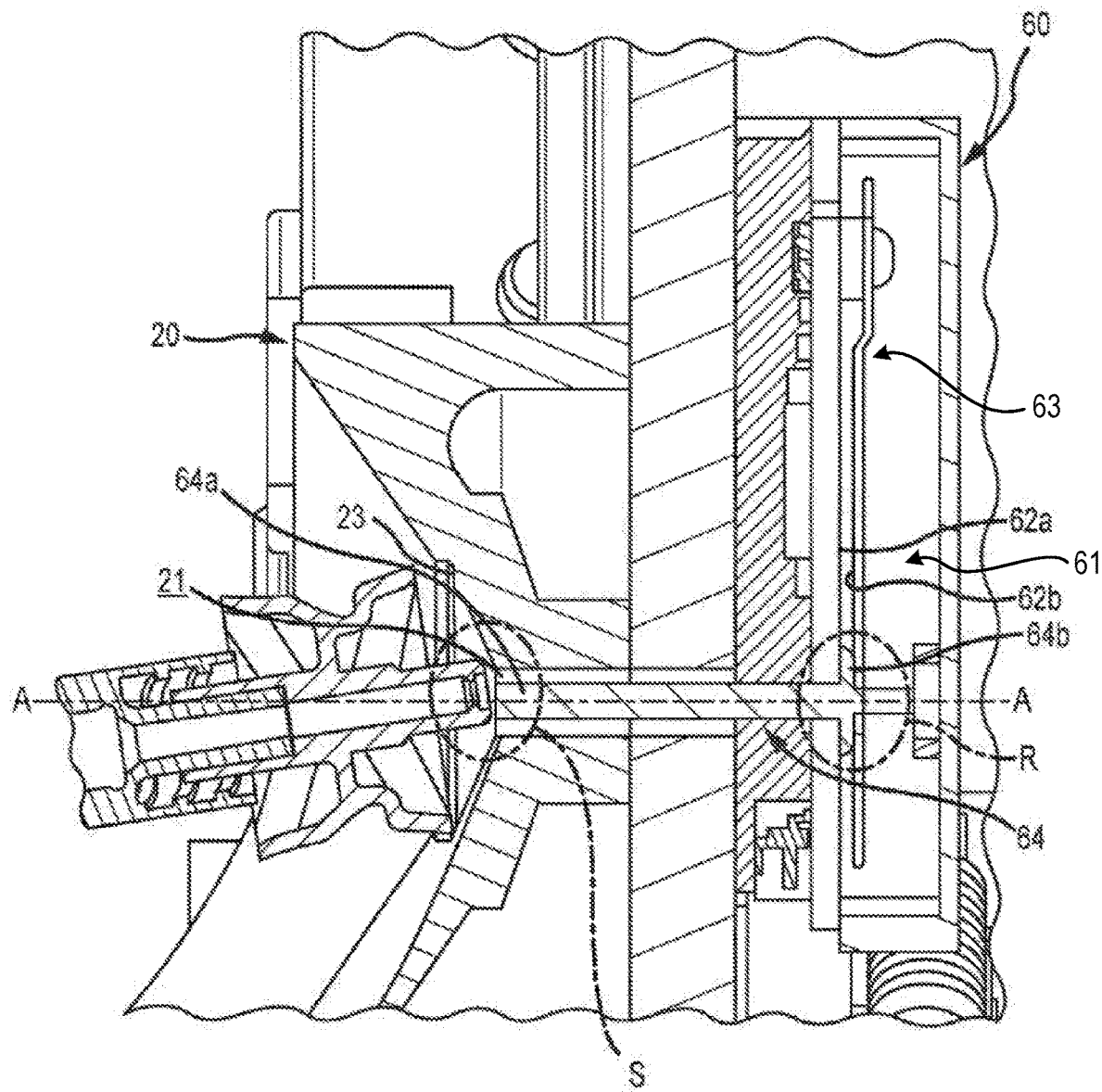
FIG. 5 is a side cross-sectional view of a first member and sensor of the syringe positioning embodiment of FIG. 1, illustrating an example of an end of a syringe improperly located relative to a predetermined location, or reference datum, on the predetermined axis AA.

In the embodiment shown in FIG. 2, the sensor (60) may comprise a capacitive sensor (e.g., capacitive sensor (61) illustrated in FIG. 5) for sensing an electrical capacitance between first and second conductive surfaces (62a), (62b). For example, the capacitive sensor may comprise a leaf spring sensor having a first conductive surface (62a) disposed on a circuit board, and a second conductive surface (62b) defined by a spring member (63) that is biased towards the first conductive surface (62a). Additionally, sensor (60) may comprise a rod member (64) having a first end (64a) located at the aperture (21) and a second end (64b) located between the first and second conductive surfaces (62a, 62b). The second end (64b) of the rod member (64) may be provided to displace the second conductive surface (62b) upon positioning of one of a syringe dispensing tip and projecting tip of a locating cap within the aperture (21) of the second member (20) at the predetermined location. In particular, and as shown in FIG. 2, the spring member (63)

defining the second conductive surface (62b) may apply a spring force to the rod member (64) so as to locate the first end (64a) thereof at the predetermined location. In turn, when the syringe dispensing tip or projecting tip of a locating cap is advanced to the predetermined location, the rod member (64) is displaced thereby displacing the second conductive surface (62b).

As indicated, the sensor (60) may provide an output signal in response to positioning of a syringe dispensing tip or a projecting tip of a locating cap within the aperture (21). In that regard, the output signal may be indicative of the presence of one of a syringe dispensing tip and a projecting tip of a locating cap when positioned at the predetermined location within the aperture (21) of the second member (20). Such predetermined location may function as a reference datum for syringe length determination and for additional syringe handling procedures to be completed after positioning of a syringe at an axially aligned position on the predetermined axis (i.e. with one end of the syringe located at the predetermined location).

In some embodiments, the output signal may also be indicative of the presence of one of a syringe dispensing tip and a projecting tip of a locating cap when positioned at a location different from the above-noted predetermined location within the aperture (21), e.g. thereby indicating misalignment of a syringe relative to the predetermined axis AA. In turn, in response to such output signal, the actuator (30) may be provided to automatically retract the first member (10) away from the second member (20), thereby allowing a syringe to drop back in to the tray, e.g. for a repeated attempt to position the syringe on the predetermined axis AA or removal from the tray.

An example of an end of a syringe improperly located relative to the predetermined location, or reference datum, is illustrated in FIG. 5. As shown, a projecting tip of a locating cap located at one end of a syringe is positioned at a location other than the predetermined location. More particularly, and with reference to the encircled region S, the rod member (64) of the sensor (60) is shown with a first end (64a) thereof biased to the predetermined location by the spring member (63) defining the second conductive surface (62b). In that regard, and as further shown by the encircled region S, an end of the projecting tip of the locating cap on the syringe is shown in a position offset from the reference datum, or predetermined location. As a result of such mispositioning, the end of the syringe has not displaced the rod member (62) to indicate proper positioning at the predetermined location, as shown in FIG. 2. In that regard, the encircled region R of FIG. 5 illustrates the second end (64b) of the rod member (64) located in a non-displaced position corresponding with positioning of the first end (64a) at the predetermined location. In conjunction with the example of FIG. 5, the output signal will be indicative of mispositioning of the syringe relative to the reference datum on the predetermined axis AA. In turn, in response to such output signal the actuator (30) may be provided to automatically retract the first member (10) away from the second member (20), as set forth above.

Figure 6:
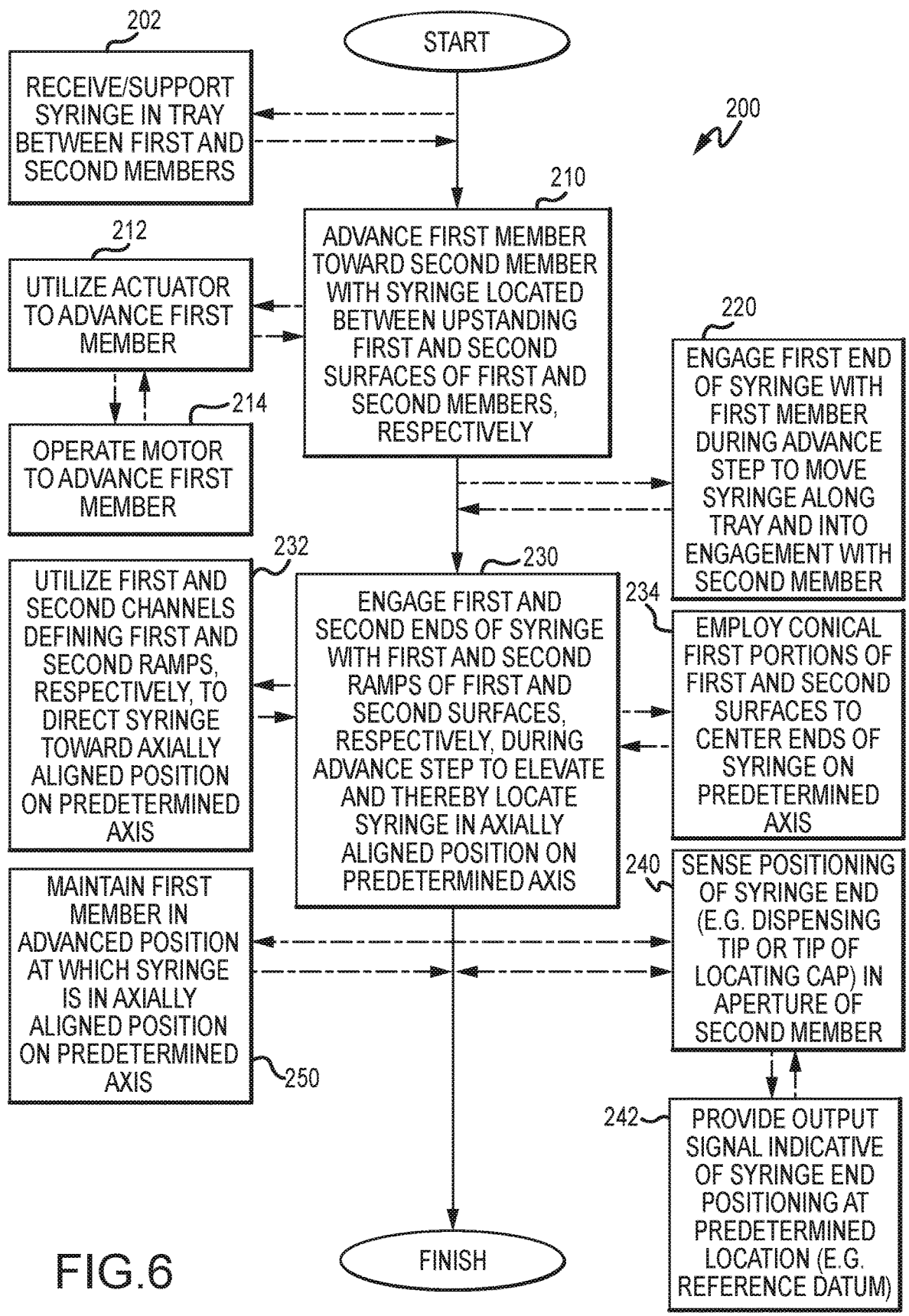
FIG. 6 is a process flow diagram of one embodiment of a syringe positioning method.

Reference is now made to FIG. 6 which syringe positioning method embodiment (200). The method embodiment (200) includes advancing a first member toward a second member with a syringe located between upstanding first and second surfaces of the first and second members, respectively (210). The method embodiment (200) further includes engaging first and second ends of the syringe with first and second ramps of the first and second surfaces, respectively, during the advancing step (210) to elevate and thereby locate the syringe in an axially aligned position on a predetermined axis (230).

The method embodiment (200) may further include receiving the syringe in a tray between the first and second members (202) prior to the advancing step (210). In conjunction with the advancing step (210) the method embodiment (200) may include engaging the first end of the syringe with the first member (220) during the advancing step (210) to move the syringe along the tray (e.g. towards and into engagement with the second member).

In some implementations, the advancing step may include the use of an actuator to advance the first member (212). In some arrangements, such actuator use may entail operation of a motor to provide a mechanical output to advance the first member (214), as described above.

In some implementations, the engaging step (230) may include utilizing first and second channels, first and second ramps, respectively, to direct first and second ends of the syringe towards the axially aligned position on the predetermined axis (232). Further, the engaging step (230) may entail the employment of conical first portions of the first and second surfaces of the first and second members, respectively, to center the first and second ends of the syringe on the predetermined axis (234).

In contemplated arrangements, the method embodiment (220) may further include sensing the positioning of a syringe dispensing tip or projecting tip of a locating cap on a syringe dispensing tip in an aperture of the second member (240). In one approach, an output signal may be provided that is indicative of sensed positioning of a projecting tip of a locating cap or a syringe dispensing tip at a predetermined location established as a reference datum (242). In that regard, the first member may be maintained in an advanced position (e.g. by the actuator) at which the syringe is located in an axially aligned position on the predetermined axis with an end thereof located at the predetermined location.

In some embodiments, the method embodiment (200) may further include the provision of an output indicative of a length of a syringe positioned in the axially aligned position on the predetermined axis AA. In that regard, such output may be provided by an actuator utilized to advance the first member, wherein the output may be further indicative of a position of the first member relative to a predetermined reference location (e.g. a home position of the first member prior to initiation of the advancing step (210)).

Figure 7:
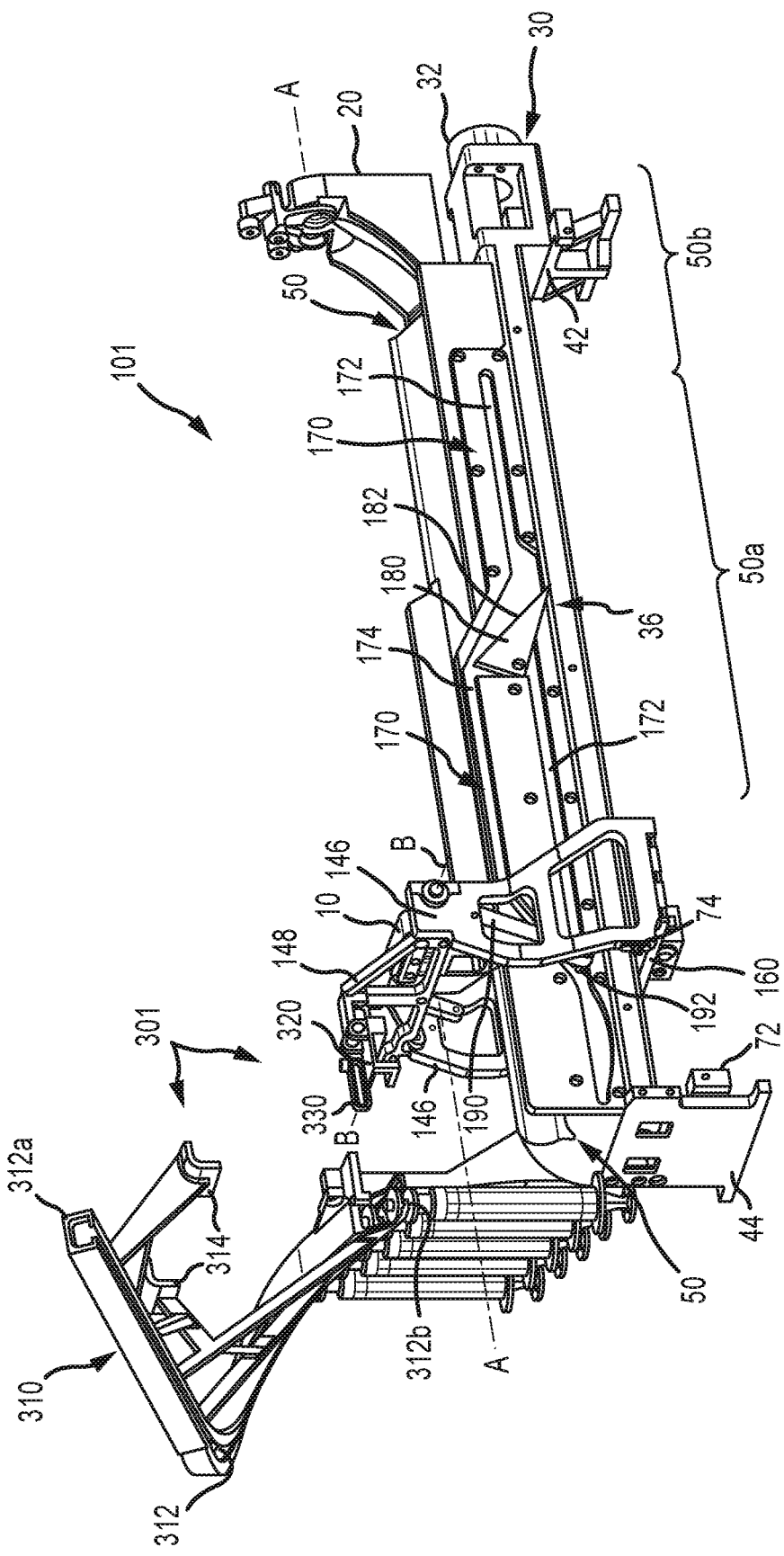
FIG. 7 is a perspective view of another embodiment of a syringe positioning apparatus that further includes an embodiment of an apparatus for syringe loading and transfer.

Reference is now made to FIG. 7 which illustrates another embodiment of a syringe positioning apparatus (101) comprising a number of components included in the syringe positioning apparatus (1) described hereinabove. As such, the common components are referenced utilizing the same corresponding reference numbers, and the descriptions of such common components provided hereinabove apply equally to the syringing positioning apparatus (101).

As shown in FIG. 7, the first member (10) may be supportably interconnected to and moveable with a modified mount member (146) operatively interconnected to actuator (30). For example, mount member (146) may be supportably interconnected to a plate member (160) that is interconnected to the linear actuator that extends through housing (36) and is operatively interconnected to electric motor (32), as described above. In that regard, the linear actuator may comprise a screw/traveling nut arrangement, wherein the plate member (160) is interconnected to the traveling nut for co-movement therewith. In turn, upon driven rotation of the linear actuator by the rotatable output shaft of the electric motor (32), the traveling nut and interconnected plate member (160), mount member (146) and first member (10) may be moved along tray (50) in a first direction toward the second member (20) from a retracted position to an advanced position, and in a second direction away from the second member (20) from an advanced position to a retracted position.

In syringe positioning apparatus (101), the first member (10) may be moveably interconnected to the mount member (146), wherein when the first member (10) is moved in the first direction toward the second member (20) the first member (10) may maintain a first orientation (e.g. a downward orientation relative to tray (50) as shown in FIG. 7), and wherein the first member may move to a different second orientation (e.g. an upward orientation relative to tray (50)) during movement in the second direction away from the second member (20). For example, in the embodiment shown in FIG. 7, a top end of the first member (10) may be pivotably interconnected to the mount member (146) at pivot axis (BB) elevated relative to the tray (50), wherein a bottom end of the first member (10) may be disposed downward in the first orientation when moved from a retracted position in the first direction towards second member (20) to an advanced position, and wherein the bottom end of the first member (10) may pivot upward to a second orientation during movement from an advanced position in the second direction away from the second member (20).

For such purposes, syringe positioning apparatus (101) may include a guide member (170) that extends along a length of the tray (50), and that includes a first guide track (172) to guide the first member (10) in the downward first orientation during movement of the first member (10) from a retracted position in the first direction toward the second member (20), and an adjoining second guide track (174) to guide the first member (10) in the upward second orientation during at least a portion of the movement of the first member (10) from an advanced position in the second direction away from the first member (10) and toward the retracted position. Further, the top end of the first member (10) may be fixedly interconnected to a carrier member (190) having a top end pivotably interconnected at pivot axis BB to mount member (146) and having at least one guide follower (192) at a cantilevered, bottom end for engagement with the first and second guide tracks (172, 174), respectively.

As shown in FIG. 7, syringe positioning apparatus (101) may also include a diverter member (180) that is disposed to divert, or guide, the first member (10) from the first orientation to the second orientation during movement of the first member (10) in the second direction away from an advanced position relative to second member (20). More particularly, the diverter member (180) may be disposed to engage the guide follower (192) during movement of the first member (10), carrier member (190) and mount member (146) from an advanced position in the second direction, thereby progressively diverting, or guiding, the guide follower (192) upward and into the second guide track (174), wherein the first member (10) progressively pivots upward and in to the second orientation. As shown in FIG. 7, the second guide track (174) may be located above and extend along a first portion of the first guide track (172), and may adjoin the first guide track (172) at opposing ends of the second guide track (174). Further, the first guide track (172) may comprise a second portion that extends beyond the second guide track (172) and diverter member (180) in the first direction toward second member (20).

The diverter member (180) may be pivotally disposed relative to the guide member (170) and located to extend across the first guide track (172) in a first position (e.g. as shown in FIG. 7), wherein during movement of the first member (10) in the first direction to an advanced position relative to second member (20), the guide follower (192) may engage and thereby pivot the diverter member (180) away from the first guide track (172) to permit passage thereby, and wherein the diverter member (180) may thereafter automatically pivot and return to the first position upon disengagement with the guide follower (192). Further, the diverter member (180) may include a ramp surface (182) that extends across the first guide track (172) when the diverter member (180) is in the first position, wherein during movement of the first member (10) from the advanced position (i.e. relative to second member (20)) in the second direction, the guide follower (192) may engage the ramp surface (182) of the diverter member (180) and thereby diverted, or guided, upward and in to a first end of the second guide track (174), whereupon the first member (10) may pivot from the first orientation to the second orientation. As shown, the second guide track (174) may be configured so that, upon continued movement of the first member (10) in the second direction along the second guide track (174), the guide follower (192) may engage the second guide track (174) so as to progressively pivot the first member (10) from the second orientation back to the first orientation. For such purposes, a second end portion of the second guide track (174) may be angled relative to and in to adjoinment with the first guide track (172).

As may be appreciated from the foregoing description, the syringe positioning apparatus (101) may be provided so that a syringe may be supportably received by the tray (50) in a first region (50a) of the tray (50), wherein during movement of the mount member (146) and first member (10) in the first direction from a retracted position the first member (10) may pass through the first region (50a) in the first orientation and thereby engage and advance a syringe along the track (50) from the first region (50a) and in to a second region (50b) of the tray (50) within which the first member (10) may reach an advanced position and cooperate with second member (20) to engage, elevate and thereby locate the syringe on the predetermined axis AA therebetween, as described hereinabove. Further, during retractive movement of the mount member (146) and first member (10) away from an advanced position in the second direction, the first member (10) may pivot from the downward first orientation to the upward second orientation and thereby bypass the first region (50a) of the tray (50). As will be further described, such capability to bypass the first region (50a) of the tray (50) facilitates positioning of one syringe in the first region (50a), while another syringe is being positioned in the second region (50b) of the tray (50) between first member (10) and second member (20) on the predetermined axis AA, as described above.

Figure 8A:
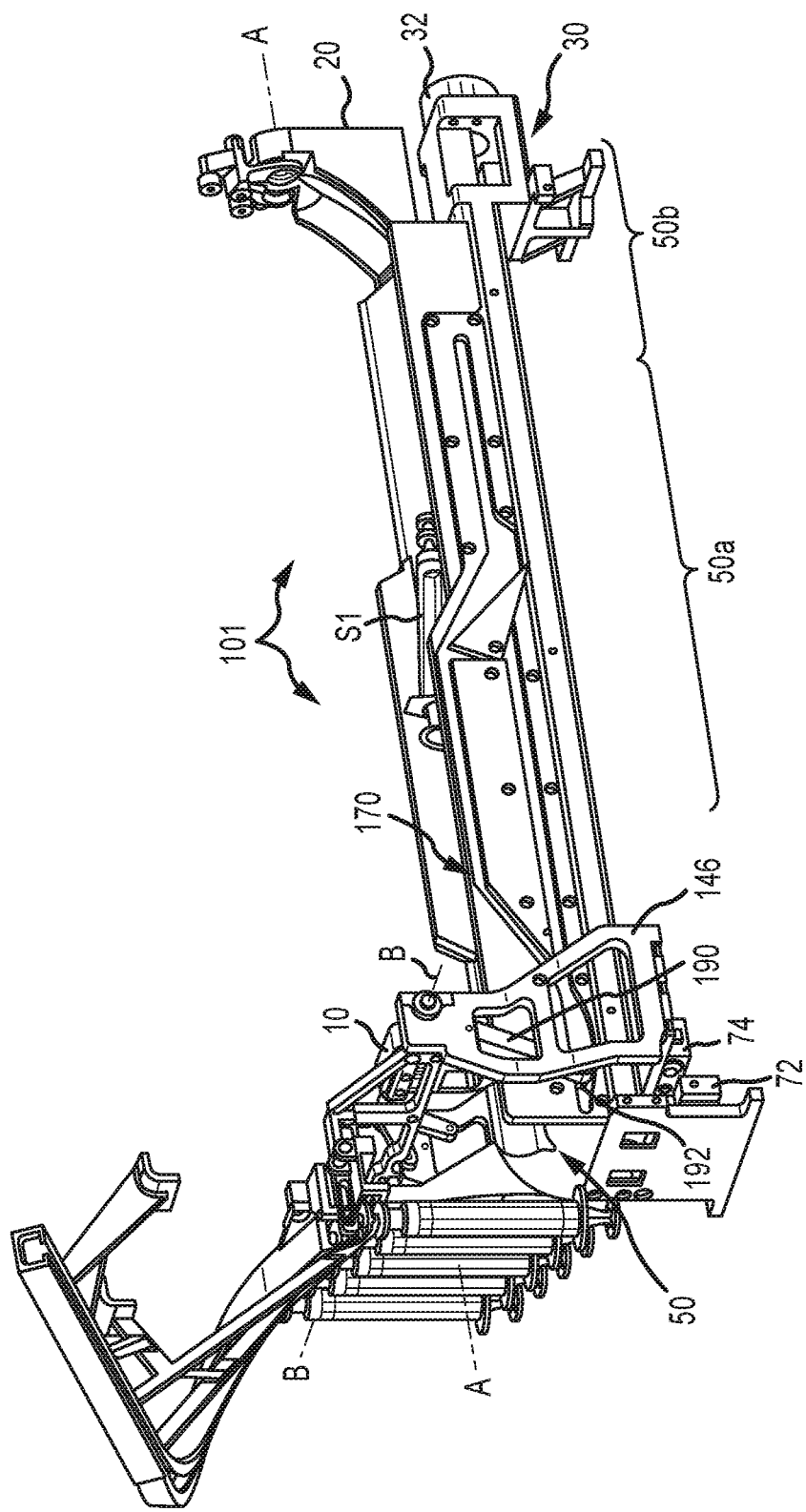
FIGS. 8A, 8B and 8C are perspective views of the syringe positioning apparatus embodiment of FIG. 7, illustrating progressive stages of movement of a mount member and first member in a first direction, and positioning of a syringe at an axially aligned position on a predetermined axis AA.
Figure 8B:
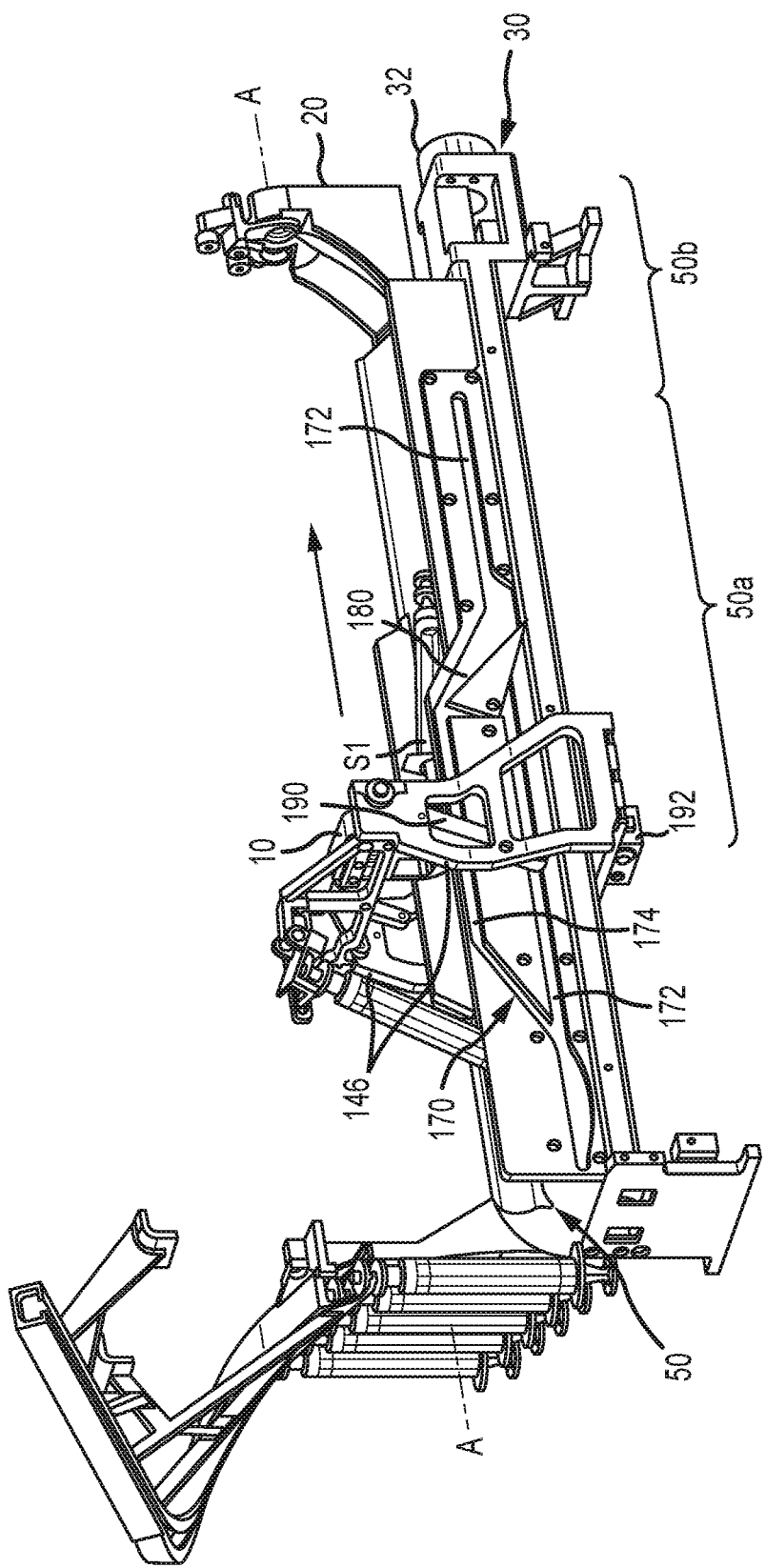
Figure 8C:
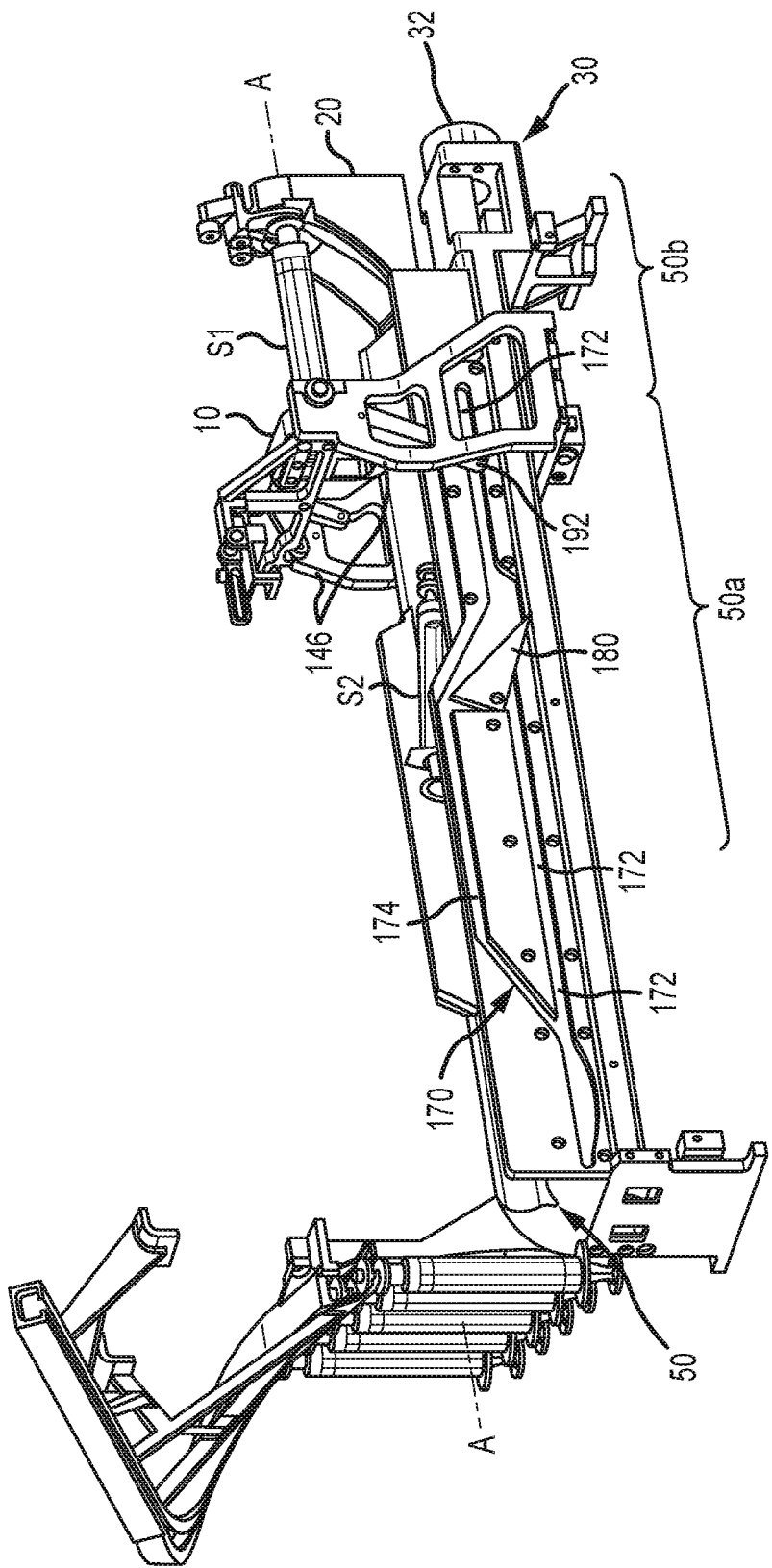

In further relation to the foregoing description, reference is now made to FIGS. 8A, 8B and 8C which illustrate progressive stages of the positioning of a first syringe (S1) on the predetermined axis AA by the syringe positioning apparatus (101). As illustrated, in FIG. 8A, the first member (10) and mount member (146) may be initially located in a retracted, or home, position relative to one end of the tray (50) with the first syringe (S1) supportably located in the first region (50a) relative to tray (50). As described above, a sensor (72) may be disposed at a fixed location adjacent to the predetermined home position of the first member (10) and a sensor tag (74) may be interconnected to the first member (10) for co-movement therewith (e.g. sensor tag (74) may be mounted to mount member (146) as shown in FIG. 7). In turn, the sensor (72) may be provided to sense whether and/or when the sensor tag (74) is located at a location that corresponds with positioning of the first member (10) at the predetermined home position, and to provide an output signal to actuator (30) in response thereto.

As shown in FIGS. 8B and 8C, the actuator (30) may be selectively operated to advance the mount member and interconnected first member (10) in the first direction toward the second member (20), wherein the first member (10) may pass through the first region (50a) in a downward orientation so as to engage and thereby advance the first syringe (S1) from the first region (50a) in to the second region (50b) relative to tray (50). As shown in FIG. 8C, the actuator (30) may be further operated to move the mounting member (146) and first member (10) in the first direction to an advanced position relative to second member (20), wherein the first member (10) and second member (20) may cooperate to engage, elevate and thereby locate the syringe on the predetermined axis AA therebetween. During or after such positioning of the first syringe (S1), and as shown in FIG. 8C, a second syringe (S2) may be received in the first region (50a) relative to tray (50). In that regard, the successive positioning of syringes (e.g. first syringe (S1) and second syringe (S2)) in the first region (50a) may be completed manually and/or in an automated manner. In the later regard, one embodiment for automated positioning of syringes in the first region (50a) will described hereinbelow.

Figure 9A:
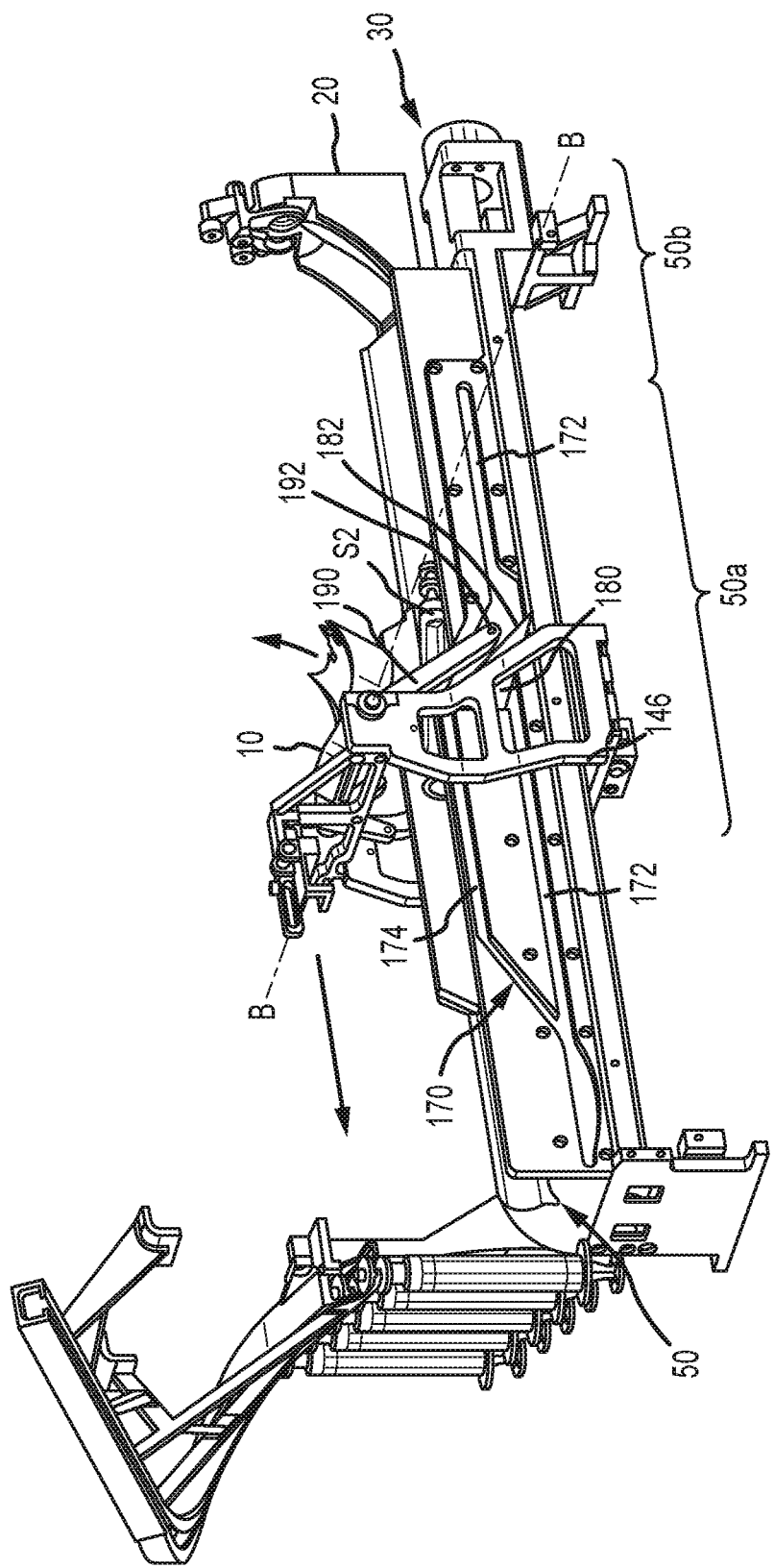
FIGS. 9A, 9B and 9C are perspective views of the syringe positioning apparatus embodiment of FIG. 7, illustrating progressive stages of movement of a mount member and first member in a second direction to bypass a first region of a tray.
Figure 9B:
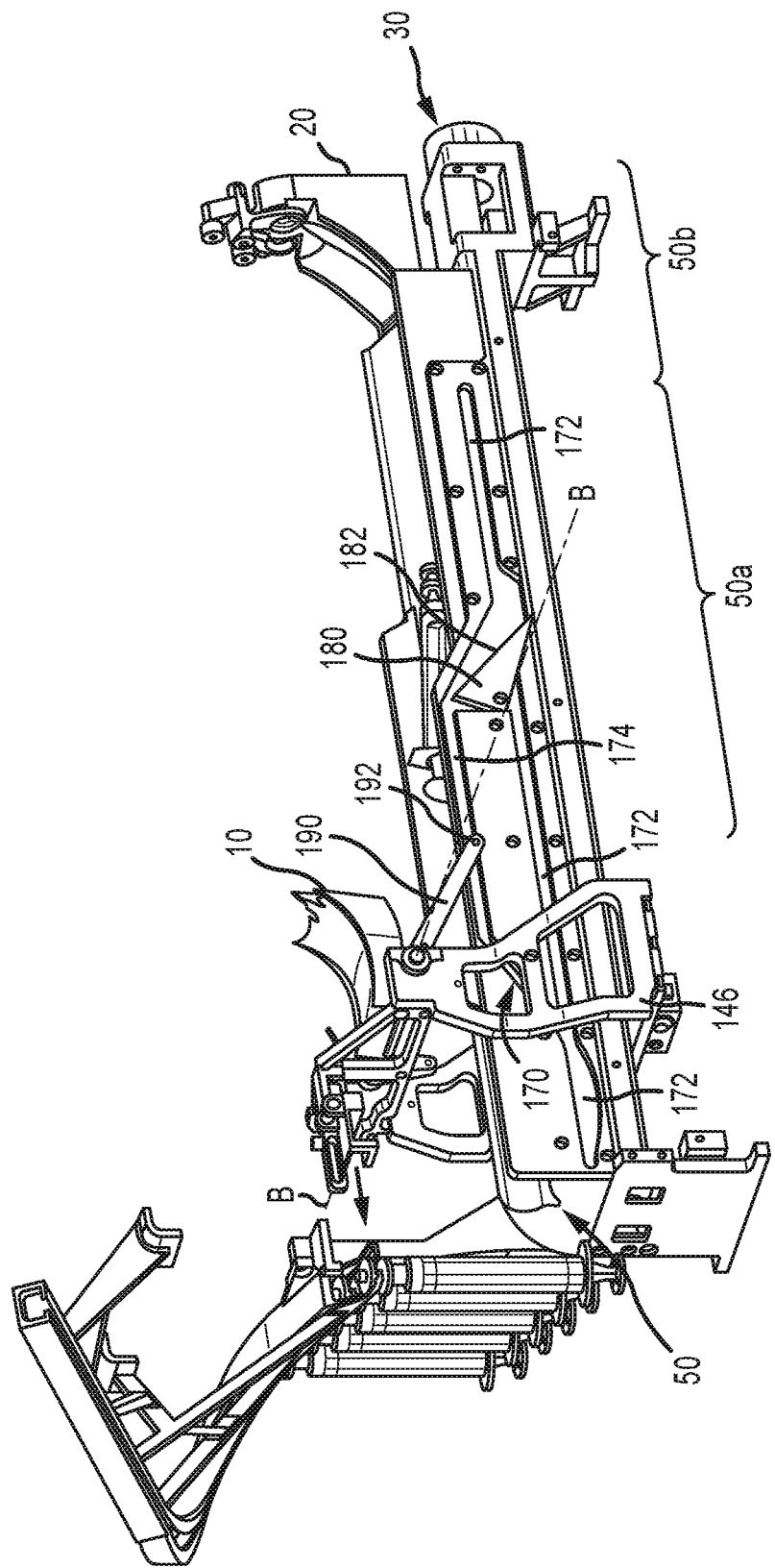
Figure 9C:
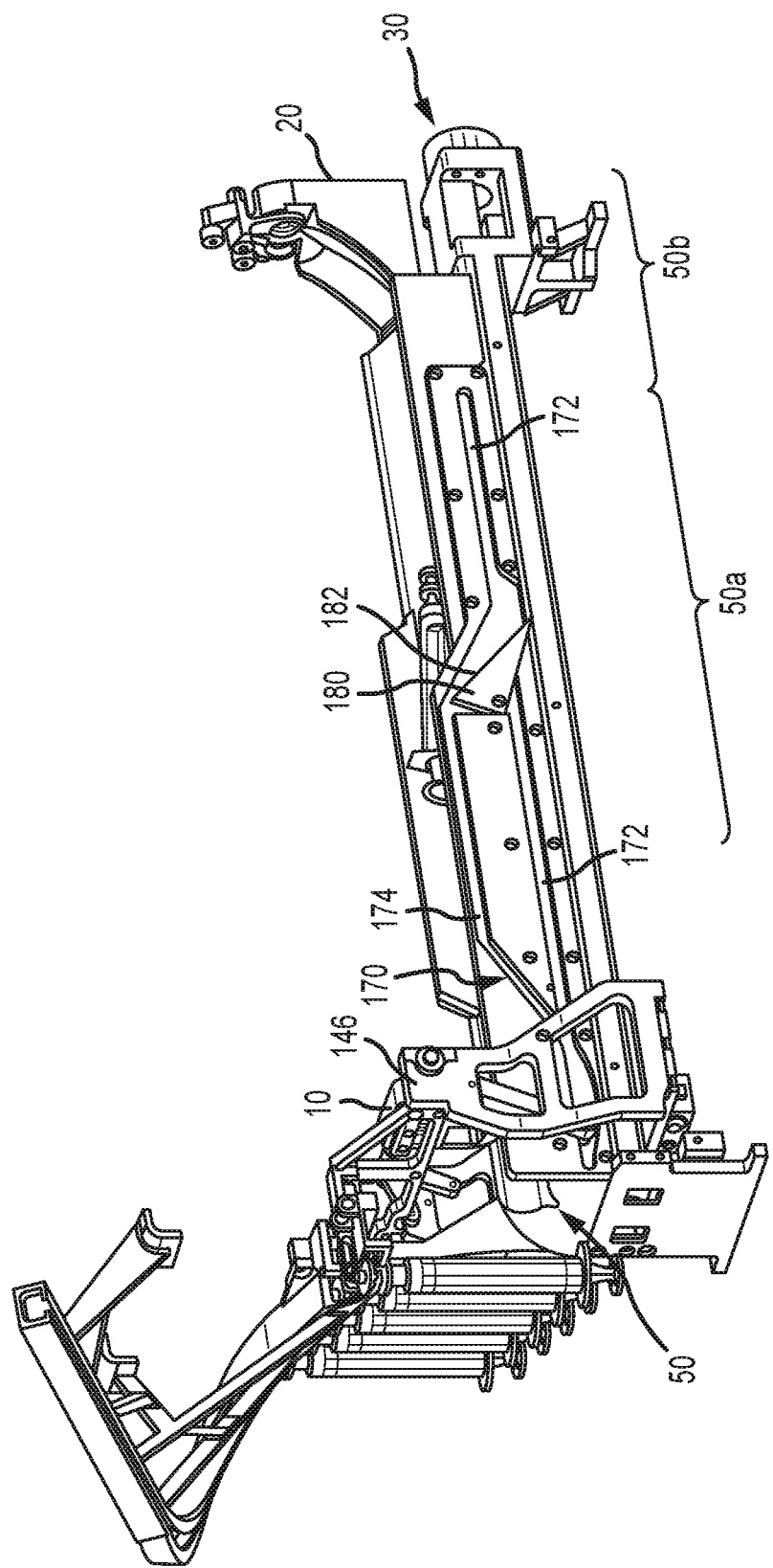

Reference is now made to FIGS. 9A, 9B and 9C which illustrate stages of movement of the mount member (146) and first member (10) in the second direction away from the advanced position shown in FIG. 8C to the home, or retracted position, shown in FIG. 8A. In particular, FIG. 9A illustrates that carrier member (146) and first member (10) have moved in the second direction from an advanced position, along and out of the second portion of first guide track (172) to a position at which guide follower (192) has engaged the ramp surface (182) of the diverter member (180) and has advanced along the ramp surface (182) so as to initiate pivotal movement of the first member (10) from the downward first orientation toward the upward second orientation. In conjunction with such movement, FIG. 9A and FIG. 9B illustrate how the first member (10) may pivot upward to bypass the first region (50a) within which the second syringe (S2) has been supportably received by tray (50).

As shown in FIG. 9B, the mounting member (146) and first member (10) have been further moved in the second direction, wherein the guide follower (192) may be guided by second guide track (174) so that the first member (10) has been pivoted to the second orientation for bypass movement over the first region (50a) within which the second syringe (S2) has been received. In FIG. 9C, the mount member (146) and first member (10) have been further moved in the second direction to a home, or retracted, position corresponding with that shown in FIG. 8A. As shown, an end region of the first portion of first guide track (172) may be of an arcuate configuration (e.g. adjacent to the home position for mount member (146) and first member (10)), extending below a longitudinal axis of the first guide track (172), thereby facilitating pivotal movement of the first member (10) from the upward first orientation back to the downward first orientation at the home position.

As noted above in relation to FIG. 7, a syringe may be supportably positioned within the first region (50a) relative to tray (50) in either a manual or automated manner. In the later regard, and with further reference to FIG. 7, an embodiment of a syringe loading and transfer apparatus (301) is illustrated. The syringe loading and transfer apparatus (301) may include a loading member (310) for supportably receiving one or a plurality of syringes as shown, and a support member (320) for receiving a syringe from the loading member (310) and transferring the syringe from the loading member (310) in the first direction, i.e. towards the second member (20), wherein the syringe may be supportably received by tray (50) in the first region (50a). The loading member (310) may be provided with one or more bracket members (314) for fixed interconnection to a support structure (not shown).

As illustrated, the loading member (310) may include a channel (312) for supportably receiving a cap located on a dispensing tip of a capped syringe at a first end (312a) of the channel (312) (e.g. via manual loading), wherein the capped syringed may be supportably suspended from the channel (312). For such purpose, the channel (312) may be of an inverted C-shaped configuration, wherein the cap of a capped syringe may be received within the channel and supported by opposing spaced flanges of the channel (312). In turn, a barrel of the suspended capped syringe may extend downward through an opening between the flanges. Similarly, the support member (320) may be provided to supportably receive a cap of the capped syringe from the loading member (310) at a first position adjacent to a second end (312b) of the channel (312), wherein the support member (320) is configured to receive and to transfer a capped syringe with the capped syringe supportably suspended therefrom. The first position of support member (320) may correspond with the positioning of the mount member (146) and first member (10) at a predetermined home position, as described hereinabove.

As may be appreciated, the capped syringe may include a locating cap, as described hereinabove. In turn, a commonly configured locating cap may be provided on the distal tips of syringes of various sizes, thereby facilitating suspended handling of each of the varying syringes by the syringe loading and transfer apparatus (301). In one embodiment, the locating cap may include an end portion having a peripheral rim, or flange, that defines a pair of 180° offset, chevron surfaces oriented towards the syringe.

The channel (312) of the loading member (310) may be angled downwardly from the first end (312a) to the second end (312b) thereof, thereby providing for automatic, gravity-induced movement of a supportably suspended, capped syringe from the first end (312a) to the second end (312b) of the channel (312). Further, the downwardly angled channel (312) may be of a helical configuration.

As noted above, the support member (320) may be provided to receive a capped syringe at the second end (312b) of the channel (312) of the loading member (310). For such purposes, the loading member (310) may be fixedly located adjacent to the home position of mount member (146) and the support member (320) may be supportably interconnected to the mount member (146) described above for co-movement therewith. Further, the syringe loading and transfer apparatus (301) may include an arm member (330) supportably and moveably interconnected to the mount member (146). In the embodiment shown in FIG. 7, the support member (320) and arm member (330) may each be supportably and moveably interconnected to a truss member (148) that is fixedly interconnected to the mount member (146) for co-movement therewith, on opposing sides of and at an elevated position relative to tray (50).

Reference is now made to FIGS. 10A-10E which illustrate the transfer of a supportably suspended syringe from a second end (312b) of channel (312) to a suspended support position on support member (320). In particular, FIGS.

10A-10C show the support member (320) having moved with mount member (146) in the second direction and approaching the first position for syringe transfer, wherein the arm member (330) is disposed transverse to an exposed, end portion of the channel (312) (e.g., an end portion comprising the opposing spaced flanges and corresponding adjoined sidewall portions), upstream from the second end (312b) of the channel (312) with the cap of a capped syringe located between the arm member (330) and the second end (312b) of the channel (312). The second end (312b) of channel (312) may comprise a seat portion configured to locate a capped syringe at a predetermined location relative to the first position to be assumed by the support member (320).

As noted above, the arm member (330) may be moveably interconnected to the mount member (146). Specifically, arm member (330) may be pivotably interconnected to the mount member (146), and more particularly to the truss member (148), for pivotable movement about an axis CC from an open orientation shown in FIGS. 10A-10C, to a closed orientation shown in FIGS. 10D and 10E, as described below. In that regard, the arm member (330) may be biased (e.g. by a spring member) to the open orientation. Further, support member (320) may be pivotably interconnected to the mount member (146), and more particularly to truss member (148), for pivotable movement about an axis DD, as further described below.

Figure 10A:
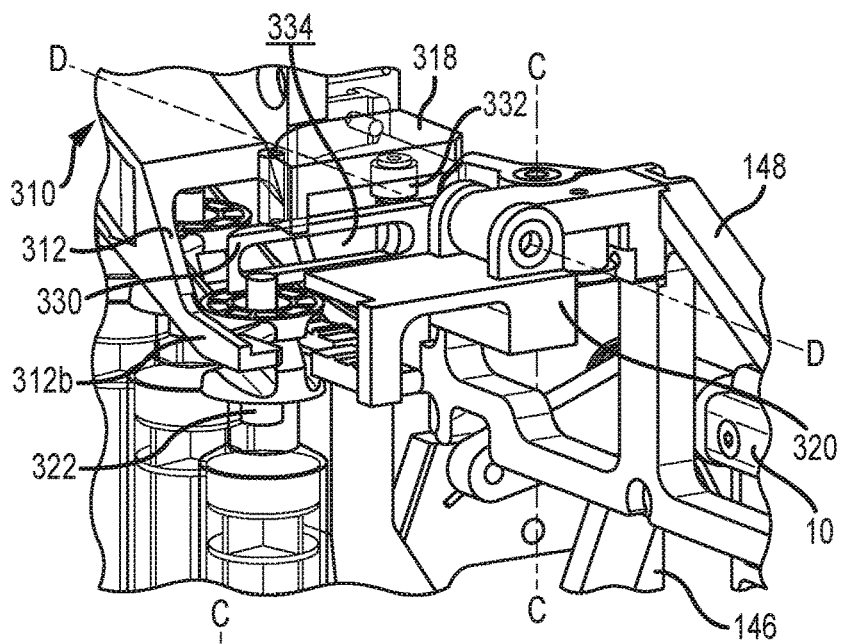
FIGS. 10A, 10B, 10C, 10D and 10E are each perspective views of a loading member and a support member of the embodiment of the apparatus for syringe loading and transfer shown in FIG. 7, illustrating the transfer of a syringe from the loading member to the support member.
Figure 10B:
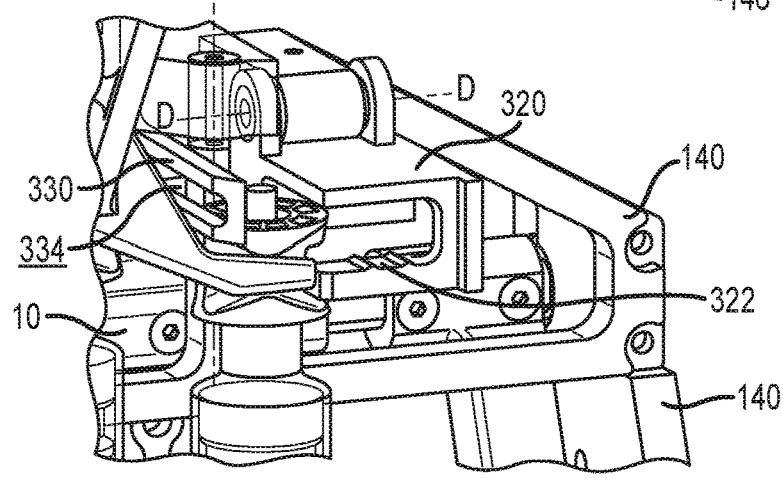
Figure 10C:
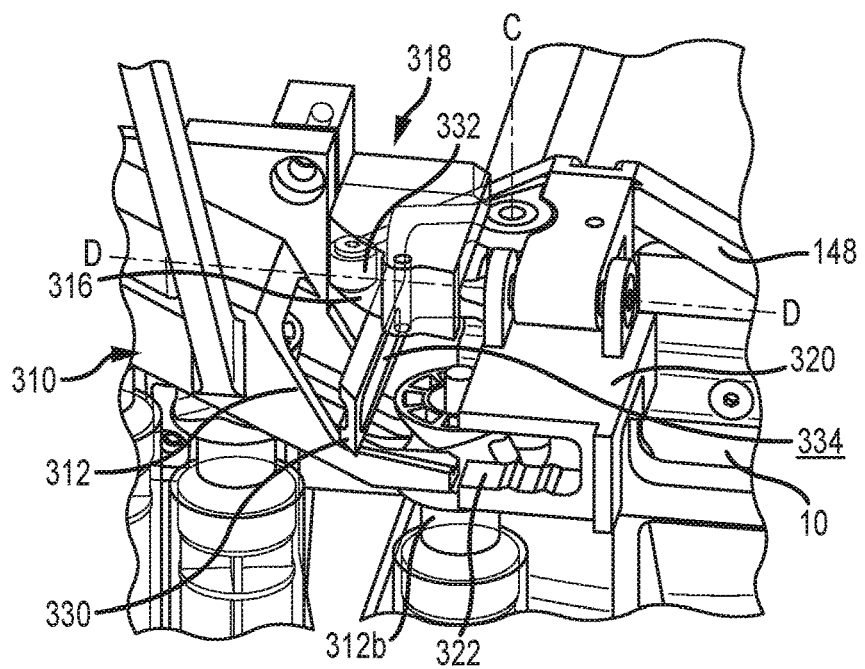
Figure 10D:
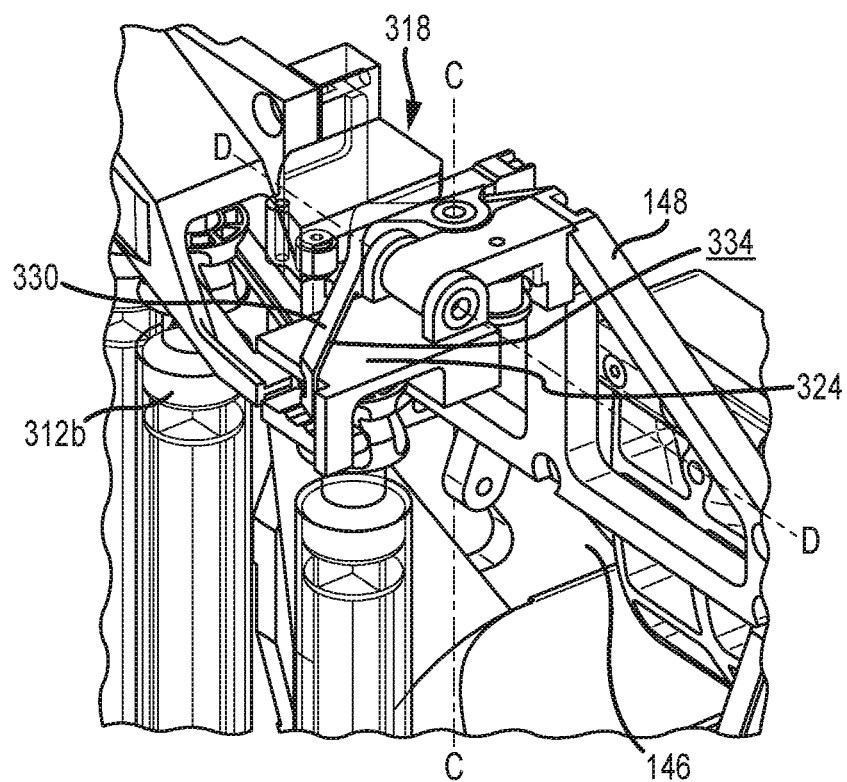
Figure 10E:
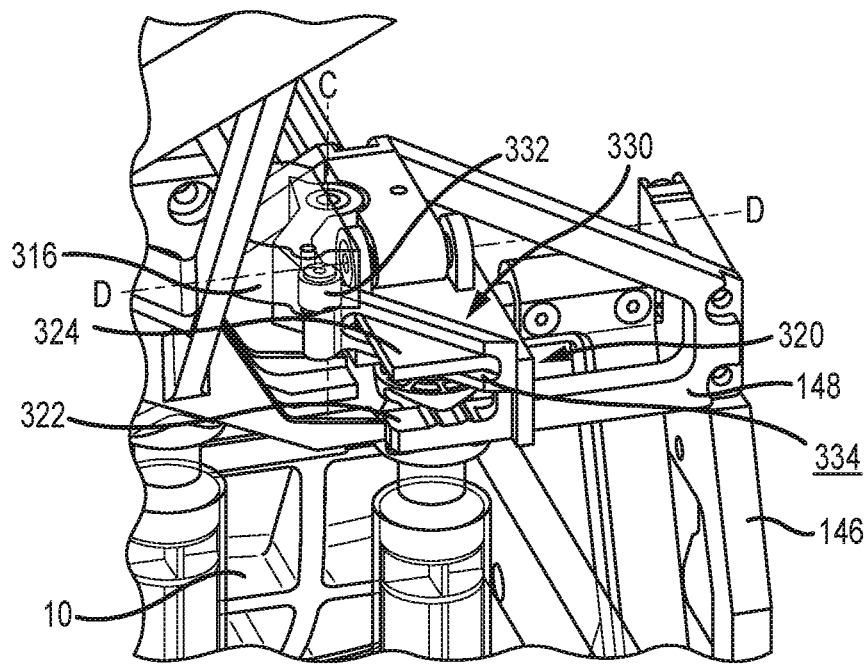

FIGS. 10D and 10E show support member (320) having further moved in the second direction in to the first position, wherein the arm member (330) has pivoted about axis CC from the open orientation shown in FIGS. 10A-10C to a closed orientation so as to engage the cap of the capped syringe and thereby move the capped syringe from the second end (312b) of the channel (312) of loading member (310) in to supported engagement with the support member (320). In the later regard, and as shown in FIGS. 10A-10E, the support member (320) may include a support seat (322) for supportably receiving a portion of the cap of the capped syringe thereupon, wherein the capped syringe is supportably suspended from the support member (320) with the barrel of the capped syringe extending through an opening of the support member (320) adjacent to the support seat (322).

To pivot the arm member (330) from the open orientation to the closed orientation, the arm member (330) may be disposed to engage a fixed surface (e.g. a contoured cam surface). In that regard, an arcuate fixed surface (316) may be defined by a cam housing (318) fixedly interconnected to loading member (310), as semi-transparently illustrated in FIGS. 10C-10E. In turn, the arm member (330) may include a cam member (332) for progressively engaging the arcuate fixed surface (314) as the support member (320) is moved in to the first position, thereby pivoting the arm member (330) to the closed orientation. Further, the arm member (330) may have an opening (334) therethrough for receiving a roof portion (324) of the support member (320) as the arm member (330) pivots to the closed orientation, thereby facilitating the desired positioning of the capped syringe relative to the support seat (322) of the support member (320) by the arm member (330). In that regard, the support seat (322) may comprise a pair of upstanding protrusions for receiving a chevron surface of a peripheral rim of a locating cap therebetween.

Figure 11A:
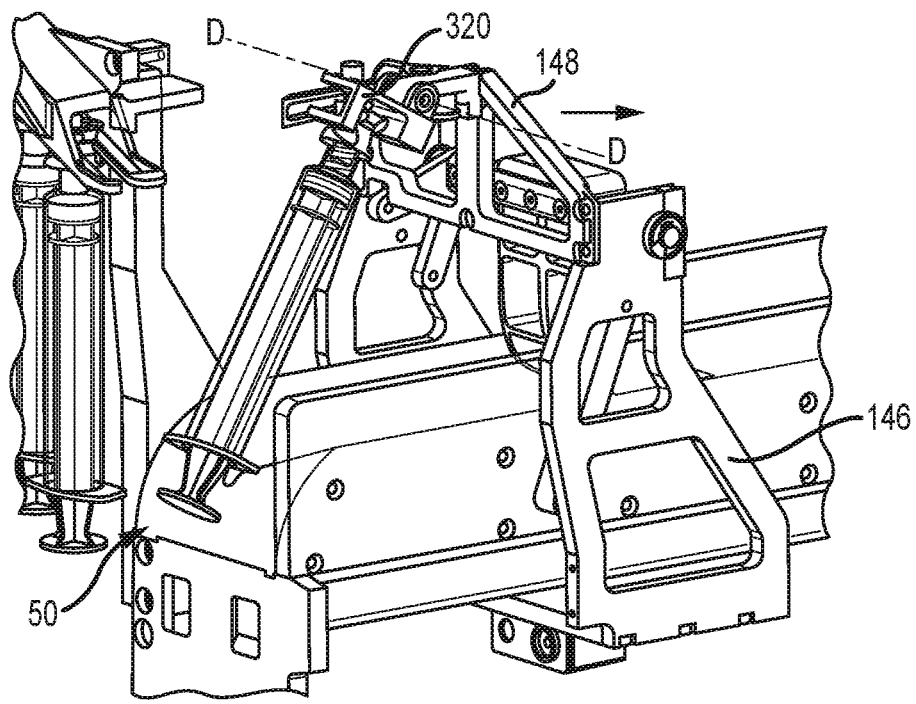
FIGS. 11A, 11B, 11C and 11D are perspective views of a support member and a tray of the embodiment of the apparatus for syringe loading and transfer shown in FIG. 7, illustrating the transfer of a syringe from the support member to the tray.

Reference is now made to FIGS. 11A-11D which illustrate the transfer of a supportably suspended syringe from the support member (320) to a supported position in the first region (50a) relative to tray (50). In particular, FIG. 11A illustrates movement of the mount member (146) in the second direction so as to move the support member (320) in the second direction from the first position relative to the loading member (310), wherein a free end of the supportably suspended syringe (i.e. an end from which a plunger projects) has engaged an end of the tray (50) (e.g. a convex, arcuately configured end). In that regard, and as noted above, the support member (320) may be pivotably interconnected to the mount member (146), and more particularly to truss member (148), for pivotal movement about axis DD. In turn, in response to the engagement of the free end of the capped syringe with the end of tray (50), as shown in FIG. 10A, the support member (320) may pivot from a support orientation to an angled, or release, orientation relative to the orientation of the support member (320) when located in the first position shown in FIGS. 10A-10C.

Figure 11B:
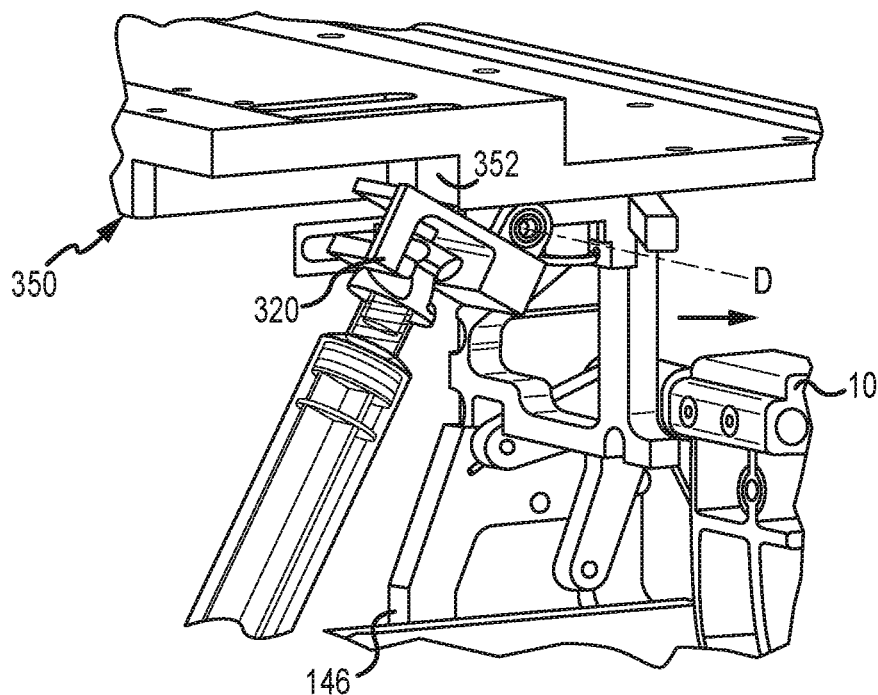
Figure 11C:
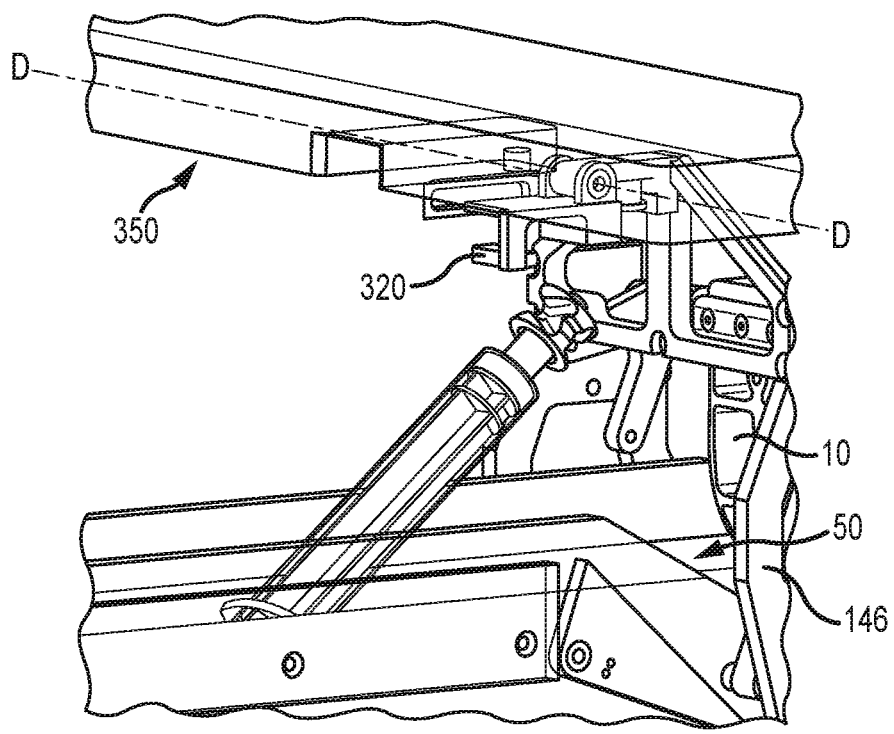
Figure 11D:
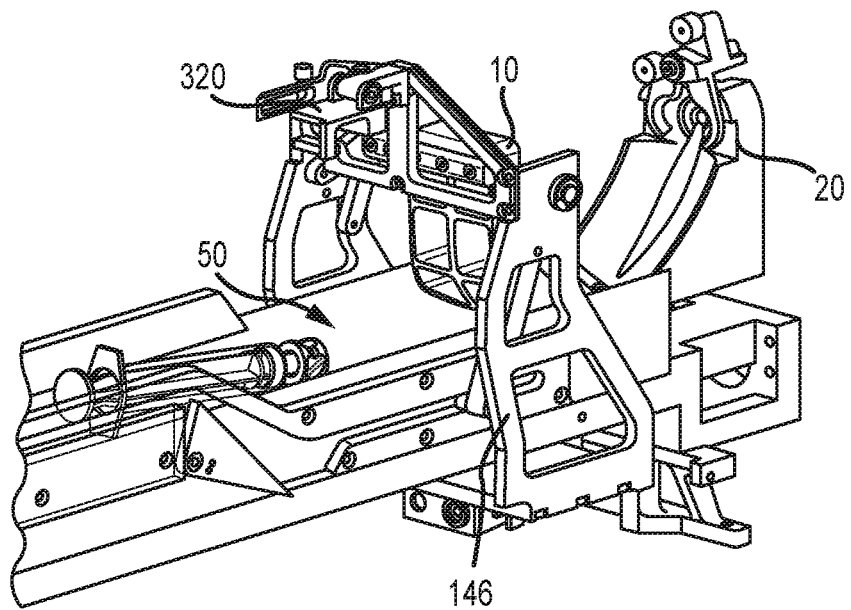

In turn, upon further movement of the mounting member (146) and interconnected support member (320) in the first direction, as shown in FIG. 11B, the angled support member (320) may be disposed to engage a fixed surface (352) defined by a support structure (350) so as to release the capped syringe from the support member (320) for receipt by the tray (50). More particularly, and as shown in FIGS. 11C and 11D, the fixed surface (352) may be located so that the angled support member (320) engages the fixed surface (352) and pivots back to the support orientation, whereupon the capped syringe may be released for supportable receipt in a reclined position in the first region (50a) of the tray (50).

As may be appreciated, the transfer of a capped syringe as shown and described in relation to FIGS. 11A-11D may be completed in overlapping, timed relation to the positioning of another syringe at an elevated, predetermined location on the predetermined axis A between the first member (10) and second member (20), as otherwise described hereinabove in relation to the syringe positioning apparatus (101). Such integrated functionality of the syringe positioning apparatus (101) and syringe loading and transfer apparatus (301) may advantageously facilitate increased syringe handling capabilities.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only preferred embodiment and variants thereof have been shown and described and that all changes and modifications that come within the spirit of the invention are desired to be protected.

What is claimed is:

1. An apparatus for syringe positioning, comprising:
a first member having an upstanding, first surface; and,
a second member having an upstanding, second surface facing the first surface of the first member, wherein the first and the second surfaces include first and second ramps, respectively, that angle upward and away from one another, wherein at least one of the first and second members is advanceable toward the other one of the first and second members, and wherein upon the advancement the first and second ramps are operable to engage, elevate and thereby locate a syringe in an axially aligned position on a single predetermined axis extending between the first and second members.

2. The apparatus of claim 1, wherein the first member is advanceable by an actuator toward the second member and the second member is disposed in a fixed location.

3. The apparatus of claim 1, wherein the first and second ramps are at least partially defined by corresponding inclined first and second channels, respectively, extending along corresponding lengths thereof.

4. The apparatus of claim 1, wherein the first surface includes a first portion having a first conical configuration centered on the predetermined axis and the second surface includes a first portion having a second conical configuration centered on the predetermined axis.

5. The apparatus of claim 1, further comprising:
a tray defining a V-shaped recession that extends from the second member towards the first member, wherein the first member is advanceable by the actuator over and along the V-shaped recession towards the second member.

6. The apparatus of claim 5, wherein the second member comprises:
an aperture located on the predetermined axis and sized to receive one of a dispensing tip and a projecting tip of a cap located on the dispensing tip of a syringe, wherein at least a portion of the second surface extends about the aperture.

7. The apparatus of claim 6, further comprising:
a sensor for sensing the positioning of one of the dispensing tip and the projecting tip of the cap located on the dispensing tip of the syringe within the aperture, and for providing an output signal in response thereto.

8. The apparatus of claim 7, wherein the output signal is indicative of the presence of one of the dispensing tip and the cap located on the dispensing tip of the syringe positioned at a predetermined location within the aperture.

9. The apparatus of claim 8, wherein the sensor comprises:
a capacitive sensor for sensing an electrical capacitance that is dependent upon a position of one of the dispensing tip and the projecting tip of the cap located on the dispensing tip of a syringe relative to the aperture.

10. The apparatus of claim 9, wherein the capacitive sensor comprises first and second conductive surfaces, and wherein the sensor further comprises:
a rod member having a first end located at the aperture and a second end located to displace at least one of the first and second conductive surfaces upon positioning of one of the dispensing tip and the projecting tip of the cap located on the dispensing tip of the syringe within the aperture.

11. The apparatus of claim 10, wherein the at least one of the first and second conductive surfaces is defined by a spring member located to bias the rod member so that the first end thereof is at the predetermined location in the aperture prior to the positioning of one of the dispensing tip and the projecting tip of the cap located on the dispensing tip of the syringe within the aperture.

12. The apparatus of claim 8, wherein the output signal is further indicative of the presence of one of the dispensing tip and the cap located on the dispensing tip of the syringe positioned at a location different from the predetermined location within the aperture.

13. The apparatus of claim 12, wherein the actuator is controllable to automatically retract the first member away from the second member when the output signal is indicative of the presence of one of the dispensing tip and the cap located on the dispensing tip of the syringe positioned at a location different from the predetermined location within the aperture.

14. The apparatus of claim 8, wherein the second surface includes a stop portion configured to conformally engage a surface of the cap located on the dispensing tip of the syringe and having the projecting tip positioned at the predetermined location within the aperture.

15. The apparatus of claim 5, further comprising:
a mount member moveable along the tray in a first direction from a retracted position and in a second direction toward the retracted position, the first member being supportably interconnected to and moveable with the mount member, wherein during movement of the mount member in the first direction from the retracted position the first member advances toward the second member and is disposed to pass through a first region of the tray to engage and thereby advance a syringe from the first region in to a second region of the tray within which the first member and second member are operable to engage, elevate and thereby locate the syringe on the predetermined axis, and wherein during movement of the mount member in the second direction toward the retracted position the first member retracts away from the second member and is disposed to bypass the first region.

16. The apparatus of claim 15, wherein the first member is moveable relative to the mount member and disposed to move from a first orientation to a second orientation for the bypass of the first region during movement of the mount member in the second direction.

17. The apparatus of claim 16, further comprising:
a guide member disposed to guide the first member in the second orientation for the bypass of the first region during movement of the mount member in the second direction.

18. The apparatus of claim 17, wherein the first member is pivotably interconnected to the mount member and disposed to pivot from the first orientation to the second orientation for the bypass of the first region during movement of the mount member in the second direction, and to pivot to the first orientation from the second orientation after the bypass of the first region during movement of the mount member in the second direction.

19. The apparatus of claim 17, wherein the first member is pivotably interconnected to the mount member at a pivot axis elevated relative to the tray, and wherein the first member is pivoted downward in the first orientation and upward in the second orientation.

20. The apparatus of claim 19, further comprising:
a carrier member supportably and pivotably interconnected to the mount member at the pivot axis, wherein the first member is interconnected in fixed relation to the pivot member for pivotable co-movement therewith.

21. The apparatus of claim 20, wherein the carrier member comprises at least one guide follower, and wherein the guide member comprises:
a first guide track to interface with the at least one guide follower to guide the first member in the first orientation for the passage through the first region and in to the second region during movement of the mount member in the first direction; and,
a second guide track to interface with the at least one guide follower to guide the pivotal movement of the first member in the second orientation for the bypass of the first region during movement of the mount member in the second direction, and to guide the pivotal movement of the first member to the first orientation from the second orientation after the bypass of the first region during movement of the mount member in the second direction.

22. The apparatus of claim 21, further comprising:
a diverter member to divert the at least one guide follower to interface with the second guide track during movement of the mount member from the second region in the second direction toward the retracted position.

23. The apparatus of claim 15, further comprising:
a support member for supportably receiving a syringe at a first position of the support member, wherein the support member is interconnected to the mount member for co-movement therewith from the first position in the first direction to transfer the syringe to the first region of the tray.

24. The apparatus of claim 23, further comprising:
a loading member for supportably receiving and successively presenting different ones of a plurality of syringes for receipt by the support member.

25. The apparatus of claim 24, further comprising:
a moveable arm member to advance a syringe from the loading member to the support member.

26. The apparatus of claim 1, wherein the first surface includes a first portion centered on the predetermined axis and the second surface has a first portion centered on the predetermined axis, the first portion of the first surface and the first portion of the second surface are configured to locate the syringe in the axially aligned position on the predetermined axis.

27. The apparatus of claim 1, wherein the first and second ramps are configured to facilitate sliding engagement of an end of the syringe up the first and second ramps thereby locating the syringe in the axially aligned position on the predetermined axis.

28. The apparatus of claim 1, wherein the first ramp is angled at a first angle, and wherein the first angle is within a range of 26.8° to 57.1° with respect to a horizontal plane.

29. The apparatus of claim 1, wherein the second ramp is angled at a second angle, and wherein the second angle is within a range of 26.8° to 57.1° with respect to a horizontal plane.

* * * * *